US007279335B2

(12) United States Patent
Sasaya et al.

(10) Patent No.: US 7,279,335 B2
(45) Date of Patent: Oct. 9, 2007

(54) NUCLEIC ACIDS ENCODING LETTUCE BIG-VEIN VIRAL PROTEINS AND UTILIZATION THEREOF

(75) Inventors: Takahide Sasaya, Kagawa (JP); Hiroki Koganezawa, Hiroshima (JP)

(73) Assignee: National Agricultural Research Organization, Ibaraki (JP)

( * ) Notice: Subject to any disclaimer, the term of this patent is extended or adjusted under 35 U.S.C. 154(b) by 800 days.

(21) Appl. No.: 10/276,968

(22) PCT Filed: May 22, 2001

(86) PCT No.: PCT/JP01/04268

§ 371 (c)(1),
(2), (4) Date: Jan. 17, 2003

(87) PCT Pub. No.: WO01/90362

PCT Pub. Date: Nov. 29, 2001

(65) Prior Publication Data

US 2004/0014032 A1    Jan. 22, 2004

(30) Foreign Application Priority Data

May 22, 2000   (JP)   ............................. 2000-154440
Mar. 8, 2001   (JP)   ............................. 2001-65339

(51) Int. Cl.
*C12N 15/82*   (2006.01)
*C12N 5/10*   (2006.01)
*C07H 21/04*   (2006.01)
*A01H 5/00*   (2006.01)
*A01H 5/10*   (2006.01)

(52) U.S. Cl. .................. 435/468; 435/320.1; 435/419; 536/23.72; 800/305; 800/278

(58) Field of Classification Search ..................... None
See application file for complete search history.

(56) References Cited

U.S. PATENT DOCUMENTS 5,684,226 A    11/1997   Sarreal

FOREIGN PATENT DOCUMENTS

WO    WO 2004/009817 A1    1/2004

OTHER PUBLICATIONS

New England Biolabs Catalog, 1996, p. 111.*
Unverified English language translation of WO 2004/009817 A1, 29 pages (Document AL1).
Co-pending Non-Provisional U.S. Appl. No. 10/521,596, Kawazu et al., filed Jan. 18, 2005.
Mirkov, T.E. and Dodds, J.A., "Association of Double-Stranded Ribonucleic Acids with Lettuce Big Vein Disease," *Phytopathology* 75:631-635, The American Phytopathological Society (1985).
Vetten, H.J. et al., "Electron Microscopical and Serological Detection of Virus-like Particles Associated with Lettuce Big Vein Disease," *J. Phytopathology 120*:53-59, Paul Parey Scientific Publishers (1987).
Baulcombe, D.C., "Mechanisms of Pathogen-Derived Resistance to Viruses in Transgenic Plants," *Plant Cell 8*:1833-1844, American Society of Plant Physiologists (1996).
Roggero, P. et al., "An Ophiovirus isolated from lettuce with big-vein symptoms," *Arch. Virol. 145*:2629-2642, Springer-Verlag (Dec. 2000).
Sasaya, T. et al., "Amino Acid Sequence of a Protein Encoded in RNA1 of Lettuce Big-vein Virus," presented at The Annual Meeting of the Phytopathological Society of Japan, Abstract No. 2-29, p. 55, Sendai, Japan (Apr. 2-4, 2001).
Sasaya, T. et al., "Nucleotide sequence of the coat protein gene of Lettuce big-vein virus," *J. Gen. Virol. 82*:1509-1515, Society for General Microbiology (Jun. 2001).
Sasaya, T. et al., "Nucleotide Sequence of the Coat Protein Gene of Lettuce Big-vein Virus," *Jpn. J. Phytopathol. 66*:298, Abstract No. 64, The Phytopathological Society of Japan (Dec. 2000).
Sasaya, T. et al., "Nucleotide Sequence of the Coat Protein of Lettuce Big-vein Virus," in the Drafts of Summaries of Speech at the Meeting of the Kansai Division of Phytopathological Society of Japan, p. 74, Abstract No. 64, Kensai, Japan (Oct. 12-13, 2000).
English translation of Sasaya, T. et al., "Amino Acid Sequence of a Protein Encoded in RNA1 of Lettuce Big-vein Virus," presented at The Annual Meeting of the Phytopathological Society of Japan, Abstract No. 2-29, p. 55, Sendai, Japan (Apr. 2-4, 2001).
English translation of Sasaya, T. et al., "Nucleotide Sequence of the Coat Protein Gene of Lettuce Big-vein Virus," *Jpn. J. Phytopathol. 66*:298, Abstract No. 64, The Phytopathological Society of Japan (Dec. 2000).
English translation of Sasaya, T. et al., "Nucleotide Sequence of the Coat Protein of Lettuce Big-vein Virus," in the Drafts of Summaries of Speech at the Meeting of the Kansai Division of Phytopathological Society of Japan, p. 74, Abstract No. 64, Kensai, Japan (Oct. 12-13, 2000).
International Search Report for International Application No. PCT/JP01/04268 mailed on Aug. 21, 2001.

* cited by examiner

*Primary Examiner*—Ashwin Mehta
(74) *Attorney, Agent, or Firm*—Sterne, Kessler, Goldstein & Fox PLLC

(57) ABSTRACT

The coat protein of lettuce big-vein virus (LBVV) was purified from highly purified LBVV, and its partial amino acid sequences were determined. An RNA encoding the coat protein of LBVV was cloned by polymerase chain reaction using primers designed based on the determined amino acid sequences information, and its primary structure was elucidated. Moreover, the present inventors succeeded not only in isolating RNA molecules of a plurality of LBVV-encoded proteins, including LBVV polymerase, by carrying out 3'RACE and 5'RACE using primers designed based on the resulting sequence information, but also in determining their primary structure. It was found that the use of these made it possible to produce lettuce resistant to LBVV and to diagnose infections with LBVV.

21 Claims, No Drawings

SEQUENCE LISTING

<160> NUMBER OF SEQ ID NOS: 16

<210> SEQ ID NO 1
<211> LENGTH: 6078
<212> TYPE: DNA
<213> ORGANISM: Lettuce Big-vein Virus

<400> SEQUENCE: 1

```
tggaacccca aaaatcataa aaaacttcta ctattttacc acccaacgat cttgaaagct      60
cctcgcggca aataacata caactgtacg tttcaaccgt tccgctattt tccaggctgt     120
tcgcattttc ttttccccta cttcgaccttt ttccctatct ccctattccc ctatttccaa    180
agactttcgg attccatcac cctataaaat ggcacacccc aaattgaaga tgctcgatgc    240
attcagtgac gtcgtggaaa tcacaggaaa gactgccggg aaagaatcct gggatgatga    300
aagcacaata gctatgccat cctataagct ttccgtactg tccgacgccg atgctgttcg    360
tgaggtgaag atcttcctga cagggctatt tgtgaggtcc tctccgaggg cgattgctgc    420
agctctcatc atgacatgga acatgaggtc tgttgatccc gtggctgtca gaatattccc    480
cgcaaaggac aagggggaag acacagcgga tgtggatgtc aagaatctgg aggtgcccgg    540
ggtcgactac atagacgcaa tggtagagac caatgtgaag gatgcttctg atatagaaat    600
tattagagcc ggagcattca tcgctgcctc cacgctcaag atgttcgcaa agtccttcac    660
tggatggact caggcttggg aacacaagca tatccaaaaa aggtatgctg atttctgtaa    720
gaccgagtat ccattcaagg aattcacgac aaacaacaag tgcgcagaga ccatgtacga    780
```

-continued

```
ggcctatcag ggtcaaaaac tgtatcaagg aactctaggc agaatcctct atgctctggg      840
agatgtggca gatccaaggc agactgagat gttgtttgat caacatcttg ccaacactgg      900
catgcacatc atcccccagt tcacaaatgc tcaactctcg atcggtgcca ccacggcggg      960
gttactaagt gccctcaact acggacagaa cttcggcact ctaatgcagc tcaaaaagct     1020
catcaacgag agtctcagca aaccaccggg tccagacaac agagcaacct ggagattcgc     1080
caggatcttt gatccatctg tctttcaaac cctccagaca aaatactgtg cagataccgt     1140
tgccatcttg gcaaacatca attccatggg aaagctatcc acagagacta gcaatcctct     1200
gaacattgct gtgctaaagc agatggcccc ggagaggaag aggtacacga gacaggtggc     1260
gaagaacatc taccatcact tcatggtggt tgccagagct ctgaacaacg acatgttcga     1320
cacagacaaa tacaagtttg tagagtccga cgatgaggag aacatgtcg caaatgaggg      1380 agagacacca gtgaaggagt gatgagggat cctactatca tatgtaaaaa acgagaaag     1440 acaactatag gtactaaact aagagagaaa ttgagacgat tatctttgac aatgacagga     1500
aggtttgtta gagatcagtc agctatgaca aaggccattg catcatctgg taaggcaggt     1560
caggaaacta ccaaacagac cacaagtgcg gaaaagttag agagtgaaaa tgcattacta     1620
tccactgtaa aggagatgaa ccagggatgg atgtctcgtc taggtgcagg caatgattat     1680
gatgagactg aggcagaccc cgctgataca tatggagata cagaagctga tctgcctcca     1740
actataaaac cggagcatat caagaaagaa actcgcaaac aagacaaggc tcttggaatc     1800
aagaatgtgg cggggacttc ggagtctgaa agaaaagctc ttaagcaatg ggatgaggat     1860
gaaaacaaga gtgatacaga gaagctggcc ttcttggcag gattcaggta ccgtcaagat     1920
cacaactctg tagtactacg tgcacagacc gagcagttga agtcccttgt ggatatcctg     1980
acctcgtctg caacctctgt gtcaagagcc gcttctgata ttgtaaatgc aaccacgatg     2040
tcgacttcca agttggctgc tgcaatcacc aaacacatcg aagttcctcc ccatgagaca     2100
ttgaccaaga tagagatgcc aaaacttcct cttatcagct cagaagctgg gtctatatct     2160
ggagtgaaga gtgttgatgg aaagtcggtc gatgaagaaa taattgacag caacaagaag     2220
gagagcacta ggatcaagga ggaggcaaag actccaaagc ctcaaatagt caccccctcct    2280 gttatcgata gtggacctat cataacagtt ggacaaatgg caagtgttct tggggggggag    2340 gttaaggata tcttagagtt ctacgagatc ggaatggaga gtttgagtc tgtagctaag     2400 gacttgggac tctcttatga aggtcttctc aggaaatacg ggggcctctc tggattgaaa     2460
ggaacattga agaagaagat caacctgctg tgaaaatcct ctgaaaagga atcctaagat     2520
gaatgttcgt ttctgtacct ctgtaccatg ctgtcgtcaa taagtaaaaa acgagaata      2580 taagtcaata tttgtcaaag tccaattctg atatcatgtc tttgaaatct gctccttacc     2640
tatctgaaat ctcggtctct aatggtgact ccgggattgg atttgatgga ggatgtgctg     2700
atccttatgc tccgtcccgg gtgccctctc gtcgttggga ttactccacc aaatgggata     2760
tgaagataac cggggcagcg agagaattca acctgtccaa acagcctgtt ctcacggggc     2820
tcatcaacag catgaggatg aagacatctc tcactcatcc cgagattcac gtggtgtgga     2880
gagggttggt tcctcctgct gtctgcagag acgatgtggt cgtgactctc aggttcaccc     2940
cggatagaag tgagaagatg ggtttgattg cccaacatac tcatggaatg catctctata     3000
tgcatcatgt gttctatccc agccacagca taagggtggg tcctggagaa ccacttccct     3060
gggccgttgg attctctgtt ccggacttct cgttagaccc caattacaca attgccgaag     3120
```

-continued

```
tgcatgttcg cctcacgggg tatttctctg agcttcctga gtacgatatt cagcgagact   3180
ctgagttgat ctccattgtc cctatggaag agcatgtaac aggatatgcc acttctgccc   3240
ctaggatccc caacactgct tgggtggccc gaggatacaa gataggagtt aatgggaaca   3300
gtctagcaaa gaagatcaaa ttcctgcagg agatcggggt ggatatagag gctctcagaa   3360
tggtgggcca gctagataac accctgaaga aggtgagtcc acgtgctata gatggatcac   3420
catctgcaga ggcgaagagt gaagctgccc gccttgtgaa tgctcatgtt aagaccctca   3480
ctgcttgaca ggaggctcag agagacaata agagatttga gatgaggatt gactccttag   3540
tcaataaatt ggatagctac acaagactgg ctcgttggtt cttgttgtcg cttcctggaa   3600
taataggagc tcttcattat ttcttccatt acgtgtcttc tctgtgatac tgattgtgtg   3660
atctttcctg ttacttgtct agatggtgtt agatgttaga gtctgtggtt tgtgatagaa   3720
gttatatttc caattctgta ttagattgtt tgttaaaaat tagaaggcca tcgtttgttt   3780
gtgtcatagt aatcggccta tatgtaaaaa acgagagtg taagctaatc ataactatta    3840
gatggacgag gaaaatgtcg acataactga ggatgaactt tctgtcattt ccgacctaga   3900
gttggattca attactcggg tggtaggcac aaacgaaatt aagacctacg aggactacaa   3960
gctggaggaa gccaactatc ttaaggtctt ggatatcatt aagaagttct ctacttcaga   4020
cacctgtgag tgttacagat gtgagctgtt cgagagagga gatatcggaa aatttctgac   4080
gaggtctgag ttctccaaac tagcagtcct ctattgggag agatgtggac gccctagaaa   4140
ctcggaagct ttggaggcat ttataggaag gcacatctgt ataagatgtg cagcctcaat   4200
ccttctgagc catcatcccg tgatcgccat gagggcggat atgagacttc gggagatata   4260
tatagagaac ggagataaac ctgcatcttc ttcggggaca ttgttctccg ccaaggggaa   4320
gggacctaga atctaatgtc ctgaaccatt tttgcaattt aaaagtatta gaaaaaacgg   4380
ttctaaagca gtacatctca tatcattgca gaagaacgtg agagccatat tcgccttctc   4440
ataatatatc ttatgctctg caagtctacc gaatccgata tctgtaacgc accaggtatt   4500
caaacattca agctcttgtg aattcaatat ggctgagaga tgcttcgaag ctgccatgac   4560
atacatgatc ccaaacaagc agagtgtgga ggtctttgaa ggtcttctag gaatattgga   4620
tcctgtccta acttctaaac atgtgcggag ggtgtaccag gagataacag tatcctttct   4680
catgatatct ctaatttccg atcaggttga ctccaagggg atcgtgagaa tgtcagatag   4740 tcaggggggat gatgatgact cattgagctc attgacctgg aattctaaga ataaactctg   4800
gggatttcta gtaaatccgg tccctatcac ctcgagtgat ctggagaaac gactaagaat   4860
ctcctgtatg atcagctcca atgcttacag aattggtaca aatgtggccc aggtcagatt   4920
tctgctcagg attgggacat ttcctcttgt tctcagcaga gaactgggat tcttatgtcc   4980
ttcctcttct cggttttccaa gtgtgatatt tgtatctcct gacaagcaga cggagatgct   5040
caggataatc tcttcttatt actctgtcgg ggatactgag gagaaaaact gctgggggat   5100
attgggagag agatatctta caaccatatc agaggatatt tctaatctgg ttgtcatggc   5160
ctttcccttc ttgcagggag cttttccactg ctcctctgtc tattatctga attttggatg   5220
taagatggca gcagagggat ttcatgccat agcccgagaa gaactcagaa tcgctctgag   5280
caatccggtc ctgtggagcg attgtcctct gaaaagggta tacgattccc tcttgcagag   5340
aattccaaca ggcgttcata tcagtcactc ggaagaaaag ggtgatccca catttttgcc   5400
attagcagaa tattgtagca gtcatgggga atgttggatc tgtggagatc ttaagctcgg   5460
tgtagatagg ggaatagggg cagatttcag acatctgtca gaaagaagga catcctctcc   5520
```

```
agatggtttg gatgctgtga tgagtgctgt ctctagaatg atatatcatc attggagcat    5580
cccatcctgg gtctctgggg catttaagat tgcaaagttc ataggagctc attaatctca    5640
cattcatatg ctcttgaaca ctatatctcc catcttttgt ctacaattaa ataagggaga    5700
gctttcatct tattagaaaa aacgatgtcc catttttgc tcagcccgat gggatatgaa     5760
gatctgtgta cataggtgga tctggaacaa gccgccatct ttttattcct aaggtatgcg    5820
aaagggacgg atgaaagaga gcgtgagatc ttccaccaac ttaaggcact tatcggaggt    5880
aaaagtcata tggtgtcctg gaatgagaag tatggaaaaa atcggatcct gtgaacattg    5940 tgaaaataa aaaagaaga tttccgggaa tgttaaaacg ttggagtcta ccagcccgct      6000
aaagcaagtt gagttctaac aaagccgtgt tagtcggggt cttgattttg atgattttgt    6060
tgtgctgtgt ttgcgacg                                                   6078
```

<210> SEQ ID NO 2
<211> LENGTH: 397
<212> TYPE: PRT
<213> ORGANISM: Lettuce Big-vein Virus

<400> SEQUENCE: 2

```
Met Ala His Pro Lys Leu Lys Met Leu Asp Ala Phe Ser Asp Val Val
  1               5                  10                  15

Glu Ile Thr Gly Lys Thr Ala Gly Lys Glu Ser Trp Asp Asp Glu Ser
             20                  25                  30

Thr Ile Ala Met Pro Ser Tyr Lys Leu Ser Val Leu Ser Asp Ala Asp
         35                  40                  45

Ala Val Arg Glu Val Lys Ile Phe Leu Thr Gly Leu Phe Val Arg Ser
     50                  55                  60

Ser Pro Arg Ala Ile Ala Ala Leu Ile Met Thr Trp Asn Met Arg
 65                  70                  75                  80

Ser Val Asp Pro Val Ala Val Arg Ile Phe Pro Ala Lys Asp Lys Gly
                 85                  90                  95

Lys Asp Thr Ala Asp Val Asp Val Lys Asn Leu Glu Val Pro Gly Val
            100                 105                 110

Asp Tyr Ile Asp Ala Met Val Glu Thr Asn Val Lys Asp Ala Ser Asp
        115                 120                 125

Ile Glu Ile Ile Arg Ala Gly Ala Phe Ile Ala Ala Ser Thr Leu Lys
    130                 135                 140

Met Phe Ala Lys Ser Phe Thr Gly Trp Thr Gln Ala Trp Glu His Lys
145                 150                 155                 160

His Ile Gln Lys Arg Tyr Ala Asp Phe Cys Lys Thr Glu Tyr Pro Phe
                165                 170                 175

Lys Glu Phe Thr Thr Asn Asn Lys Cys Ala Glu Thr Met Tyr Glu Ala
            180                 185                 190

Tyr Gln Gly Gln Lys Leu Tyr Gln Gly Thr Leu Gly Arg Ile Leu Tyr
        195                 200                 205

Ala Leu Gly Asp Val Ala Asp Pro Arg Gln Thr Glu Met Leu Phe Asp
    210                 215                 220

Gln His Leu Ala Asn Thr Gly Met His Ile Ile Pro Gln Phe Thr Asn
225                 230                 235                 240

Ala Gln Leu Ser Ile Gly Ala Thr Thr Ala Gly Leu Leu Ser Ala Leu
                245                 250                 255

Asn Tyr Gly Gln Asn Phe Gly Thr Leu Met Gln Leu Lys Lys Leu Ile
            260                 265                 270
```

-continued

```
Asn Glu Ser Leu Ser Lys Pro Pro Gly Pro Asp Asn Arg Ala Thr Trp
        275                 280                 285

Arg Phe Ala Arg Ile Phe Asp Pro Ser Val Phe Gln Thr Leu Gln Thr
    290                 295                 300

Lys Tyr Cys Ala Asp Thr Val Ala Ile Leu Ala Asn Ile Asn Ser Met
305                 310                 315                 320

Gly Lys Leu Ser Thr Glu Thr Ser Asn Pro Leu Asn Ile Ala Val Leu
                325                 330                 335

Lys Gln Met Ala Pro Glu Arg Lys Arg Tyr Thr Arg Gln Val Ala Lys
            340                 345                 350

Asn Ile Tyr His His Phe Met Val Val Ala Arg Ala Leu Asn Asn Asp
        355                 360                 365

Met Phe Asp Thr Asp Lys Tyr Lys Phe Val Glu Ser Asp Asp Glu Glu
    370                 375                 380

Glu His Val Ala Asn Glu Gly Glu Thr Pro Val Lys Glu
385                 390                 395

<210> SEQ ID NO 3
<211> LENGTH: 333
<212> TYPE: PRT
<213> ORGANISM: Lettuce Big-vein Virus

<400> SEQUENCE: 3

Met Thr Gly Arg Phe Val Arg Asp Gln Ser Ala Met Thr Lys Ala Ile
  1               5                  10                  15

Ala Ser Ser Gly Lys Ala Gly Gln Glu Thr Thr Lys Gln Thr Thr Ser
             20                  25                  30

Ala Glu Lys Leu Glu Ser Glu Asn Ala Leu Leu Ser Thr Val Lys Glu
         35                  40                  45

Met Asn Gln Gly Trp Met Ser Arg Leu Gly Ala Gly Asn Asp Tyr Asp
     50                  55                  60

Glu Thr Glu Ala Asp Pro Ala Asp Thr Tyr Gly Asp Thr Glu Ala Asp
 65                  70                  75                  80

Leu Pro Pro Thr Ile Lys Pro Glu His Ile Lys Lys Glu Thr Arg Lys
                 85                  90                  95

Gln Asp Lys Ala Leu Gly Ile Lys Asn Val Ala Gly Thr Ser Glu Ser
            100                 105                 110

Glu Arg Lys Ala Leu Lys Gln Trp Asp Glu Asp Glu Asn Lys Ser Asp
        115                 120                 125

Thr Glu Lys Leu Ala Phe Leu Ala Gly Phe Arg Tyr Arg Gln Asp His
    130                 135                 140

Asn Ser Val Val Leu Arg Ala Gln Thr Glu Gln Leu Lys Ser Leu Val
145                 150                 155                 160

Asp Ile Leu Thr Ser Ser Ala Thr Ser Val Ser Arg Ala Ala Ser Asp
                165                 170                 175

Ile Val Asn Ala Thr Thr Met Ser Thr Ser Lys Leu Ala Ala Ala Ile
            180                 185                 190

Thr Lys His Ile Glu Val Pro Pro His Glu Thr Leu Thr Lys Ile Glu
        195                 200                 205

Met Pro Lys Leu Pro Leu Ile Ser Ser Glu Ala Gly Ser Ile Ser Gly
    210                 215                 220

Val Lys Ser Val Asp Gly Lys Ser Val Asp Glu Glu Ile Ile Asp Ser
225                 230                 235                 240

Asn Lys Lys Glu Ser Thr Arg Ile Lys Glu Glu Ala Lys Thr Pro Lys
```

```
                    245                 250                 255
Pro Gln Ile Val Thr Pro Val Ile Asp Ser Gly Pro Ile Ile Thr
            260                 265                 270
Val Gly Gln Met Ala Ser Val Leu Gly Gly Glu Val Lys Asp Ile Leu
            275                 280                 285
Glu Phe Tyr Glu Ile Gly Met Glu Lys Phe Glu Ser Val Ala Lys Asp
            290                 295                 300
Leu Gly Leu Ser Tyr Glu Gly Leu Leu Arg Lys Tyr Gly Gly Leu Ser
305                 310                 315                 320
Gly Leu Lys Gly Thr Leu Lys Lys Lys Ile Asn Leu Leu
                325                 330

<210> SEQ ID NO 4
<211> LENGTH: 290
<212> TYPE: PRT
<213> ORGANISM: Lettuce Big-vein Virus

<400> SEQUENCE: 4

Met Ser Leu Lys Ser Ala Pro Tyr Leu Ser Glu Ile Ser Val Ser Asn
1               5                   10                  15
Gly Asp Ser Gly Ile Gly Phe Asp Gly Gly Cys Ala Asp Pro Tyr Ala
                20                  25                  30
Pro Ser Arg Val Pro Ser Arg Arg Trp Asp Tyr Ser Thr Lys Trp Asp
            35                  40                  45
Met Lys Ile Thr Gly Ala Ala Arg Glu Phe Asn Leu Ser Lys Gln Pro
        50                  55                  60
Val Leu Thr Gly Leu Ile Asn Ser Met Arg Met Lys Thr Ser Leu Thr
65                  70                  75                  80
His Pro Glu Ile His Val Val Trp Arg Gly Leu Val Pro Pro Ala Val
                85                  90                  95
Cys Arg Asp Asp Val Val Val Thr Leu Arg Phe Thr Pro Asp Arg Ser
                100                 105                 110
Glu Lys Met Gly Leu Ile Ala Gln His Thr His Gly Met His Leu Tyr
            115                 120                 125
Met His His Val Phe Tyr Pro Ser His Ser Ile Arg Val Gly Pro Gly
        130                 135                 140
Glu Pro Leu Pro Trp Ala Val Gly Phe Ser Val Pro Asp Phe Ser Leu
145                 150                 155                 160
Asp Pro Asn Tyr Thr Ile Ala Glu Val His Val Arg Leu Thr Gly Tyr
                165                 170                 175
Phe Ser Glu Leu Pro Glu Tyr Asp Ile Gln Arg Asp Ser Glu Leu Ile
            180                 185                 190
Ser Ile Val Pro Met Glu Glu His Val Thr Gly Tyr Ala Thr Ser Ala
        195                 200                 205
Pro Arg Ile Pro Asn Thr Ala Trp Val Ala Arg Gly Tyr Lys Ile Gly
    210                 215                 220
Val Asn Gly Asn Ser Leu Ala Lys Lys Ile Lys Phe Leu Gln Glu Ile
225                 230                 235                 240
Gly Val Asp Ile Glu Ala Leu Arg Met Val Gly Gln Leu Asp Asn Thr
                245                 250                 255
Leu Lys Lys Val Ser Pro Arg Ala Ile Asp Gly Ser Pro Ser Ala Glu
            260                 265                 270
Ala Lys Ser Glu Ala Ala Arg Leu Val Asn Ala His Val Lys Thr Leu
        275                 280                 285
```

Thr Ala
    290

<210> SEQ ID NO 5
<211> LENGTH: 164
<212> TYPE: PRT
<213> ORGANISM: Lettuce Big-vein Virus

<400> SEQUENCE: 5

Met Asp Glu Glu Asn Val Asp Ile Thr Glu Asp Leu Ser Val Ile
  1               5                  10                  15

Ser Asp Leu Glu Leu Asp Ser Ile Thr Arg Val Val Gly Thr Asn Glu
                 20                  25                  30

Ile Lys Thr Tyr Glu Asp Tyr Lys Leu Glu Glu Ala Asn Tyr Leu Lys
             35                  40                  45

Val Leu Asp Ile Ile Lys Lys Phe Ser Thr Ser Asp Thr Cys Glu Cys
         50                  55                  60

Tyr Arg Cys Glu Leu Phe Glu Arg Gly Asp Ile Gly Lys Phe Leu Thr
 65                  70                  75                  80

Arg Ser Glu Phe Ser Lys Leu Ala Val Leu Tyr Trp Glu Arg Cys Gly
                 85                  90                  95

Arg Pro Arg Asn Ser Glu Ala Leu Glu Ala Phe Ile Gly Arg His Ile
                100                 105                 110

Cys Ile Arg Cys Ala Ala Ser Ile Leu Leu Ser His His Pro Val Ile
            115                 120                 125

Ala Met Arg Ala Asp Met Arg Leu Arg Glu Ile Tyr Ile Glu Asn Gly
        130                 135                 140

Asp Lys Pro Ala Ser Ser Ser Gly Thr Leu Phe Ser Ala Lys Gly Lys
145                 150                 155                 160

Gly Pro Arg Ile

<210> SEQ ID NO 6
<211> LENGTH: 368
<212> TYPE: PRT
<213> ORGANISM: Lettuce Big-vein Virus

<400> SEQUENCE: 6

Met Ala Glu Arg Cys Phe Glu Ala Ala Met Thr Tyr Met Ile Pro Asn
  1               5                  10                  15

Lys Gln Ser Val Glu Val Phe Glu Gly Leu Leu Gly Ile Leu Asp Pro
                 20                  25                  30

Val Leu Thr Ser Lys His Val Arg Arg Val Tyr Gln Glu Ile Thr Val
             35                  40                  45

Ser Phe Leu Met Ile Ser Leu Ile Ser Asp Gln Val Asp Ser Lys Gly
         50                  55                  60

Ile Val Arg Met Ser Asp Ser Gln Gly Asp Asp Asp Ser Leu Ser
 65                  70                  75                  80

Ser Leu Thr Trp Asn Ser Lys Asn Lys Leu Trp Gly Phe Leu Val Asn
                 85                  90                  95

Pro Val Pro Ile Thr Ser Ser Asp Leu Glu Lys Arg Leu Arg Ile Ser
                100                 105                 110

Cys Met Ile Ser Ser Asn Ala Tyr Arg Ile Gly Thr Asn Val Ala Gln
            115                 120                 125

Val Arg Phe Leu Leu Arg Ile Gly Thr Phe Pro Leu Val Leu Ser Arg
        130                 135                 140

Glu Leu Gly Phe Leu Cys Pro Ser Ser Ser Arg Phe Pro Ser Val Ile

-continued

```
                145                 150                 155                 160
Phe Val Ser Pro Asp Lys Gln Thr Glu Met Leu Arg Ile Ile Ser Ser
                    165                 170                 175
Tyr Tyr Ser Val Gly Asp Thr Glu Lys Asn Cys Trp Gly Ile Leu
                180                 185                 190
Gly Glu Arg Tyr Leu Thr Thr Ile Ser Glu Asp Ile Ser Asn Leu Val
                195                 200                 205
Val Met Ala Phe Pro Phe Leu Gln Gly Ala Phe His Cys Ser Ser Val
            210                 215                 220
Tyr Tyr Leu Asn Phe Gly Cys Lys Met Ala Ala Glu Gly Phe His Ala
225                 230                 235                 240
Ile Ala Arg Glu Glu Leu Arg Ile Ala Leu Ser Asn Pro Val Leu Trp
                245                 250                 255
Ser Asp Cys Pro Leu Lys Arg Val Tyr Asp Ser Leu Leu Gln Arg Ile
                260                 265                 270
Pro Thr Gly Val His Ile Ser His Ser Glu Glu Lys Gly Asp Pro Thr
            275                 280                 285
Phe Leu Pro Leu Ala Glu Tyr Cys Ser Ser His Arg Glu Cys Trp Ile
        290                 295                 300
Cys Gly Asp Leu Lys Leu Gly Val Asp Arg Gly Ile Gly Ala Asp Phe
305                 310                 315                 320
Arg His Leu Ser Glu Arg Arg Thr Ser Ser Pro Asp Gly Leu Asp Ala
                325                 330                 335
Val Met Ser Ala Val Ser Arg Met Ile Tyr His His Trp Ser Ile Pro
            340                 345                 350
Ser Trp Val Ser Gly Ala Phe Lys Ile Ala Lys Phe Ile Gly Ala His
            355                 360                 365

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (21)
<223> OTHER INFORMATION: i

<400> SEQUENCE: 7
garwsntggg aygaygarws nac                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
```

```
<221> NAME/KEY: modified_base
<222> LOCATION: (21)
<223> OTHER INFORMATION: i

<400> SEQUENCE: 8
gcrtcdatrt artcnacncc ngg                                          23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i

<400> SEQUENCE: 9
aayytngarg tnccnggngt nga                                          23

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10 gttttttgacc ctgatag                                                17

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11
gtcgactcta gacacttgtt gtttgtcgtg                                   30

<210> SEQ ID NO 12
<211> LENGTH: 6793
<212> TYPE: DNA
<213> ORGANISM: Lettuce Big-vein Virus
<220> FEATURE:
<221> NAME/KEY: CDS
<222> LOCATION: (337)..(6459)

<400> SEQUENCE: 12
cgagacgcat attcatacta aaattccaac aaatcaaaac cttttaacgc ccgataaaca      60
```

-continued

```
gcctttcgtc gaggcattca gcgaccctat cgtttctgtt ttgatgaatg ttgtgtattt    120
tatgttttcc gtgtttccat catccgattt tttccagatt tccctatctc caggttcttg    180
agacccttat ttctcttctt tcttctatta ctccctatcc ccgtaaccct taggattctg    240
aaccgttcag actctgagag taggatatac gtaaaaaaac gagaacaaaa ttcgctttta    300
aacattataa tatttagtaa gaactaagac aacgaa atg tct cta gca agc aga    354
                                       Met Ser Leu Ala Ser Arg
                                         1               5 atg aca agt gtt gga ggg gct gac aat tac gga gaa tcg gat tac gga    402
Met Thr Ser Val Gly Gly Ala Asp Asn Tyr Gly Glu Ser Asp Tyr Gly
             10                  15                  20 tgg gat gag act gtt tta ggg gat atg cat ctt aac agc gcg atc aac    450
Trp Asp Glu Thr Val Leu Gly Asp Met His Leu Asn Ser Ala Ile Asn
         25                  30                  35 ttg gat cta ttc aag gag ttc cta cac ata gat ccc ccc gtt tac aag    498
Leu Asp Leu Phe Lys Glu Phe Leu His Ile Asp Pro Pro Val Tyr Lys
     40                  45                  50 gtc aag gaa aat cac agg tta aca gaa gag cta aga gaa ctt caa tcc    546
Val Lys Glu Asn His Arg Leu Thr Glu Glu Leu Arg Glu Leu Gln Ser
 55                  60                  65                  70 ctg gcc aga aag ggc tca aag ata gag atc ggg ttt cag aga ctg ttt    594
Leu Ala Arg Lys Gly Ser Lys Ile Glu Ile Gly Phe Gln Arg Leu Phe
                 75                  80                  85 gct cgc atg ttc ccc aga gac gga aat ctc ata ccc atg gat agc acg    642
Ala Arg Met Phe Pro Arg Asp Gly Asn Leu Ile Pro Met Asp Ser Thr
             90                  95                 100 atg acc aga atg ata atg aag ata atc aga gac tcg ggt acc aaa tac    690
Met Thr Arg Met Ile Met Lys Ile Ile Arg Asp Ser Gly Thr Lys Tyr
        105                 110                 115 aag ctg gga atc cca ctg ctt gga atc tcg gag gaa atg atc aag aaa    738
Lys Leu Gly Ile Pro Leu Leu Gly Ile Ser Glu Glu Met Ile Lys Lys
    120                 125                 130 ggg gcc atg gtt ccc agc aac ctc gta tat agc ttc aac tgc ttt ctc    786
Gly Ala Met Val Pro Ser Asn Leu Val Tyr Ser Phe Asn Cys Phe Leu
135                 140                 145                 150 aac atc ata tac ggg aga tca gaa tgg ata agg tca gaa ggt att gcc    834
Asn Ile Ile Tyr Gly Arg Ser Glu Trp Ile Arg Ser Glu Gly Ile Ala
                155                 160                 165 att cgt ttc aaa atg tat gaa cat gga cga ttc atc agg aga gac ttg    882
Ile Arg Phe Lys Met Tyr Glu His Gly Arg Phe Ile Arg Arg Asp Leu
            170                 175                 180 acg atc agc gag aaa gag tac aac ttc atc gtc ggg aag gag gtg gtc    930
Thr Ile Ser Glu Lys Glu Tyr Asn Phe Ile Val Gly Lys Glu Val Val
        185                 190                 195 gag ata aga gca tcg agg aga aag gag aga ttc ata gca gat tac aac    978
Glu Ile Arg Ala Ser Arg Arg Lys Glu Arg Phe Ile Ala Asp Tyr Asn
    200                 205                 210 tct ctc tta ctg ctg ttg gat gtt gca gga caa cga ata tgt gca cat   1026
Ser Leu Leu Leu Leu Leu Asp Val Ala Gly Gln Arg Ile Cys Ala His
215                 220                 225                 230 cta tgt tct cag ctc ggg gaa ata tcc ggt gtt cca ggt tca ctc tct   1074
Leu Cys Ser Gln Leu Gly Glu Ile Ser Gly Val Pro Gly Ser Leu Ser
                235                 240                 245 cga tac cat ctg gag act cta tgt act gcc ggg gat aga atg ata gaa   1122
Arg Tyr His Leu Glu Thr Leu Cys Thr Ala Gly Asp Arg Met Ile Glu
            250                 255                 260 aga tgc ggt aac aag gca tac gag gtt cta gga atg tat gag gct ctc   1170
Arg Cys Gly Asn Lys Ala Tyr Glu Val Leu Gly Met Tyr Glu Ala Leu
```

-continued

```
            265                 270                 275
tgc gtg gga agg ctc ttg gaa aac aac cca gac gga ata aca gac cat    1218
Cys Val Gly Arg Leu Leu Glu Asn Asn Pro Asp Gly Ile Thr Asp His
        280                 285                 290 aca cag ttc tct gcg aac tgt gaa gag gaa cta cag gag cta att gcc    1266
Thr Gln Phe Ser Ala Asn Cys Glu Glu Glu Leu Gln Glu Leu Ile Ala
295                 300                 305                 310 ggg tct gtc gaa cca gca ttc atg aag agt cag gtg gat ttg atc aaa    1314
Gly Ser Val Glu Pro Ala Phe Met Lys Ser Gln Val Asp Leu Ile Lys
                315                 320                 325 act aca ctg gag aag atg aaa aat cag gat ata tcg aac gct ttc tgt    1362
Thr Thr Leu Glu Lys Met Lys Asn Gln Asp Ile Ser Asn Ala Phe Cys
            330                 335                 340 cta tac aga gtc tgg gga cat cca aca gtg gac ata tat gag ggg atg    1410
Leu Tyr Arg Val Trp Gly His Pro Thr Val Asp Ile Tyr Glu Gly Met
        345                 350                 355 aaa aaa gtg cat act ata ggg aca aaa gtg aag gtg att cct ccg aat    1458
Lys Lys Val His Thr Ile Gly Thr Lys Val Lys Val Ile Pro Pro Asn
360                 365                 370 cta gga aca atc atg gta tgc caa ttc agg aag atg ttc atg tca acc    1506
Leu Gly Thr Ile Met Val Cys Gln Phe Arg Lys Met Phe Met Ser Thr
375                 380                 385                 390 ttc ttc aag aag cat cat agg tac cca ccc atc acg gga acc cca gga    1554
Phe Phe Lys Lys His His Arg Tyr Pro Pro Ile Thr Gly Thr Pro Gly
                395                 400                 405 gaa tat cta gag aga tgt cta aag gac aat gtc gcg atc agg ata gag    1602
Glu Tyr Leu Glu Arg Cys Leu Lys Asp Asn Val Ala Ile Arg Ile Glu
            410                 415                 420 cac ctt gca tac aat cta aga gac ttc gag ttc atc aga ata ggg gag    1650
His Leu Ala Tyr Asn Leu Arg Asp Phe Glu Phe Ile Arg Ile Gly Glu
        425                 430                 435 aca tac agt gtt cca gac aca ttc gat atg tgt cat gtg ctc aat gac    1698
Thr Tyr Ser Val Pro Asp Thr Phe Asp Met Cys His Val Leu Asn Asp
440                 445                 450 aaa gca gtc agt ccc gac atg tca gag ctc tta gag tca ata aag aac    1746
Lys Ala Val Ser Pro Asp Met Ser Glu Leu Leu Glu Ser Ile Lys Asn
455                 460                 465                 470 ggg aaa gga act agt tgt gga gca aaa aga agg gga ata ttg aga tgg    1794
Gly Lys Gly Thr Ser Cys Gly Ala Lys Arg Arg Gly Ile Leu Arg Trp
                475                 480                 485 atg gag gga gac agt ctg aac tgt aaa tca ttt ctc tca gac att gat    1842
Met Glu Gly Asp Ser Leu Asn Cys Lys Ser Phe Leu Ser Asp Ile Asp
            490                 495                 500 gaa aag gga ctg agc gag gag gat ctt ctg ata gga atg tat gag aag    1890
Glu Lys Gly Leu Ser Glu Glu Asp Leu Leu Ile Gly Met Tyr Glu Lys
        505                 510                 515 gag cga gag atc aag gtt gct gct aga atg tac tct ctg atg aca gag    1938
Glu Arg Glu Ile Lys Val Ala Ala Arg Met Tyr Ser Leu Met Thr Glu
520                 525                 530 agg atg aga tac tat ttt gtc ttg act gaa ggg ctc att gca gac tac    1986
Arg Met Arg Tyr Tyr Phe Val Leu Thr Glu Gly Leu Ile Ala Asp Tyr
535                 540                 545                 550 ata ctg ccc cat ttc cct gag atc aca atg aag gac agc ctg aac gta    2034
Ile Leu Pro His Phe Pro Glu Ile Thr Met Lys Asp Ser Leu Asn Val
                555                 560                 565 tta ctg aag aag atg tgg gag tct gga gga cag aga agt ata gga tca    2082
Leu Leu Lys Lys Met Trp Glu Ser Gly Gly Gln Arg Ser Ile Gly Ser
            570                 575                 580 atg gat gtg aac ata aac atc gac ttc tcc aag tgg aat aca aac atg    2130
```

```
            Met Asp Val Asn Ile Asn Ile Asp Phe Ser Lys Trp Asn Thr Asn Met
                    585                 590                 595 aga gaa ggg ccc acc agt gac aca ttc aga gag atg gac gga ata ttt            2178
Arg Glu Gly Pro Thr Ser Asp Thr Phe Arg Glu Met Asp Gly Ile Phe
            600                 605                 610 ggg ttc aaa agg ttg ata gcc aga aca cat gag atc ttc aat gca tct            2226
Gly Phe Lys Arg Leu Ile Ala Arg Thr His Glu Ile Phe Asn Ala Ser
615                 620                 625                 630 ctg gtc tat tca gca tca ggg aag tac ctt cct acc atc gag gac ggt            2274
Leu Val Tyr Ser Ala Ser Gly Lys Tyr Leu Pro Thr Ile Glu Asp Gly
                635                 640                 645 aga atc cta gat gat cct ccc atg tgt tac aga ggg cac cta gga ggg            2322
Arg Ile Leu Asp Asp Pro Pro Met Cys Tyr Arg Gly His Leu Gly Gly
            650                 655                 660 ttc gag ggg ctg agg cag aag gga tgg aca gta gca act gta tgc ttg            2370
Phe Glu Gly Leu Arg Gln Lys Gly Trp Thr Val Ala Thr Val Cys Leu
        665                 670                 675 ctc gca tat ctc tca gag cag aac aag atc cag atg aag ttg atg gga            2418
Leu Ala Tyr Leu Ser Glu Gln Asn Lys Ile Gln Met Lys Leu Met Gly
    680                 685                 690 cag ggt gac aat cag atc atc agg cta agg atg ccg acc agc tac tgg            2466
Gln Gly Asp Asn Gln Ile Ile Arg Leu Arg Met Pro Thr Ser Tyr Trp
695                 700                 705                 710 gat agc tta cga ctc aca gag gag atg aag aag aag gag gcc agg att            2514
Asp Ser Leu Arg Leu Thr Glu Glu Met Lys Lys Lys Glu Ala Arg Ile
                715                 720                 725 cta tct gac aag ttc gtg cat gag atg gac ata ata ttc aca gga gta            2562
Leu Ser Asp Lys Phe Val His Glu Met Asp Ile Ile Phe Thr Gly Val
            730                 735                 740 gga ctt ccg atc aag gtc aga gag aca tgg aaa tcg aca cga ctt ttc            2610
Gly Leu Pro Ile Lys Val Arg Glu Thr Trp Lys Ser Thr Arg Leu Phe
        745                 750                 755 atg tac gga aag gta atg cta tta gac gga cgg cag ctc cct caa tgg            2658
Met Tyr Gly Lys Val Met Leu Leu Asp Gly Arg Gln Leu Pro Gln Trp
    760                 765                 770 tat aag aaa act ctc aga tca tat gct cta agc aat gag gga acc ctg            2706
Tyr Lys Lys Thr Leu Arg Ser Tyr Ala Leu Ser Asn Glu Gly Thr Leu
775                 780                 785                 790 aca atc agt ggg gtg atc gga acc atc gct acc aac atg tgt gcg gca            2754
Thr Ile Ser Gly Val Ile Gly Thr Ile Ala Thr Asn Met Cys Ala Ala
                795                 800                 805 gga gga gga agt gaa gtg ccc tgt gtt atg tat ctc ttc ttc ttg ttg            2802
Gly Gly Gly Ser Glu Val Pro Cys Val Met Tyr Leu Phe Phe Leu Leu
            810                 815                 820 ttg gcg gag tgg tca ctc gag ttc atg ttc agg tat cat ccg ttc aca            2850
Leu Ala Glu Trp Ser Leu Glu Phe Met Phe Arg Tyr His Pro Phe Thr
        825                 830                 835 agg gtt ggg atc aag gat ggg agt tca atg gag ttt cga ctg aac gag            2898
Arg Val Gly Ile Lys Asp Gly Ser Ser Met Glu Phe Arg Leu Asn Glu
    840                 845                 850 aag gga gga tat gtt cat aag cag act cga aag aca aac aat ctg tgg            2946
Lys Gly Gly Tyr Val His Lys Gln Thr Arg Lys Thr Asn Asn Leu Trp
855                 860                 865                 870 ctg aag tcc ctc ttg gtc cta gtg cct act gcc gtg gga gga agt gtt            2994
Leu Lys Ser Leu Leu Val Leu Val Pro Thr Ala Val Gly Gly Ser Val
                875                 880                 885 act att cct ctc acc gga ttc ata atg aga gga ttt cct gac aaa gct            3042
Thr Ile Pro Leu Thr Gly Phe Ile Met Arg Gly Phe Pro Asp Lys Ala
            890                 895                 900
```

|  |  |
|---|---|
| tca gag ggt tat gcg tgg ctg aaa ttc tta ggg tca tca aag tct cct<br>Ser Glu Gly Tyr Ala Trp Leu Lys Phe Leu Gly Ser Ser Lys Ser Pro<br>905                    910                    915 | 3090 |
| atc cag ggc ttc ctg aag aac ttc tat acc ttc ctt ccc aac gat acc<br>Ile Gln Gly Phe Leu Lys Asn Phe Tyr Thr Phe Leu Pro Asn Asp Thr<br>    920                    925                    930 | 3138 |
| gta gaa gcc gac atg tta gtg cag tcc cct ttc tct ctg aac cat aag<br>Val Glu Ala Asp Met Leu Val Gln Ser Pro Phe Ser Leu Asn His Lys<br>935                    940                    945                    950 | 3186 |
| aga cct cca aca ccc ggg tta caa acg aaa gag aac ata aga gaa tgg<br>Arg Pro Pro Thr Pro Gly Leu Gln Thr Lys Glu Asn Ile Arg Glu Trp<br>                955                    960                    965 | 3234 |
| ctg ctt tca aca ccg aga ttc aa cag aac cga ttc att cga agc atg<br>Leu Leu Ser Thr Pro Arg Phe Gln Gln Asn Arg Phe Ile Arg Ser Met<br>    970                    975                    980 | 3282 |
| cag gtt ctc cta tca ggg ttt gac aag aaa agt gtt tgc cgt gaa ctc<br>Gln Val Leu Leu Ser Gly Phe Asp Lys Lys Ser Val Cys Arg Glu Leu<br>985                    990                    995 | 3330 |
| cta acg gag aga atg aat ccg ctg atc agt cac gaa gtc tat gag acc<br>Leu Thr Glu Arg Met Asn Pro Leu Ile Ser His Glu Val Tyr Glu Thr<br>                1000                 1005                1010 | 3378 |
| ttt ggg cat gtt tac tgt gag ggg atc gta gcc agg gta gag aac act<br>Phe Gly His Val Tyr Cys Glu Gly Ile Val Ala Arg Val Glu Asn Thr<br>1015                 1020                 1025                1030 | 3426 |
| cga acg ata cga aca ctt cat ctc agc aga gag gac aga aag cca atc<br>Arg Thr Ile Arg Thr Leu His Leu Ser Arg Glu Asp Arg Lys Pro Ile<br>                1035                 1040                 1045 | 3474 |
| gtg gca aag cta atg act gat gag atg gca tac ata gca tat atg tgg<br>Val Ala Lys Leu Met Thr Asp Glu Met Ala Tyr Ile Ala Tyr Met Trp<br>                1050                 1055                1060 | 3522 |
| tgg agg ggg aat act aag ggt gaa gtt ttt gag gaa tgt gca aca aag<br>Trp Arg Gly Asn Thr Lys Gly Glu Val Phe Glu Glu Cys Ala Thr Lys<br>                1065                 1070                1075 | 3570 |
| cag gct cgg aaa ggt aga aat gtt ggc tgg aaa aga gag atc atg gga<br>Gln Ala Arg Lys Gly Arg Asn Val Gly Trp Lys Arg Glu Ile Met Gly<br>1080                 1085                 1090 | 3618 |
| att acc aca cct cat cct ctg gaa gtg cta ttc caa agt gta tgc aga<br>Ile Thr Thr Pro His Pro Leu Glu Val Leu Phe Gln Ser Val Cys Arg<br>1095                 1100                 1105                1110 | 3666 |
| cct ggg gac caa tgc caa aga tca gat gac tac atc aca tcg aag ctt<br>Pro Gly Asp Gln Cys Gln Arg Ser Asp Asp Tyr Ile Thr Ser Lys Leu<br>                1115                 1120                1125 | 3714 |
| gta gac gac ggg aag ttt ccc cca ttc ctt ggg agc aag atc aag aac<br>Val Asp Asp Gly Lys Phe Pro Pro Phe Leu Gly Ser Lys Ile Lys Asn<br>                1130                 1135                1140 | 3762 |
| aag gtg tac tcg ctg cag gac gaa gaa gcg aga aga gaa cca ctg atc<br>Lys Val Tyr Ser Leu Gln Asp Glu Glu Ala Arg Arg Glu Pro Leu Ile<br>                1145                 1150                1155 | 3810 |
| aaa acc ggg gct aga ttg gcc aga cag ttc aat tgg atc gga atg gga<br>Lys Thr Gly Ala Arg Leu Ala Arg Gln Phe Asn Trp Ile Gly Met Gly<br>1160                 1165                 1170 | 3858 |
| gag aat atg aga gga ttg gtc tta aag aat gta ggg tcc ata tgc gat<br>Glu Asn Met Arg Gly Leu Val Leu Lys Asn Val Gly Ser Ile Cys Asp<br>1175                 1180                 1185                1190 | 3906 |
| gtg tca gta ttt gac aag ttc gtt gat gat gat ccc tca gac aac cta<br>Val Ser Val Phe Asp Lys Phe Val Asp Asp Asp Pro Ser Asp Asn Leu<br>                1195                 1200                1205 | 3954 |
| tac act ggg tct ctc atg cac agg ttt acc ccc tcc tct gtc tct gaa<br>Tyr Thr Gly Ser Leu Met His Arg Phe Thr Pro Ser Ser Val Ser Glu<br>1210                 1215                 1220 | 4002 |

```
ggc tgc ttc atc aac tat gca cct caa gtc ggt cac aag gtc ttc atg    4050
Gly Cys Phe Ile Asn Tyr Ala Pro Gln Val Gly His Lys Val Phe Met
        1225                1230                1235 tct tca gat aca ctc ccc tct ctc tcc aga ggc cag aca aac tac aca    4098
Ser Ser Asp Thr Leu Pro Ser Leu Ser Arg Gly Gln Thr Asn Tyr Thr
    1240                1245                1250 ttt cat ttc caa gca atg tac tgc ttt ctt caa tac agc ata tcc aaa    4146
Phe His Phe Gln Ala Met Tyr Cys Phe Leu Gln Tyr Ser Ile Ser Lys
1255                1260                1265                1270 tca ggg aat gaa gga tca tac cat cat cat atc atg tgc caa gac tgt    4194
Ser Gly Asn Glu Gly Ser Tyr His His His Ile Met Cys Gln Asp Cys
            1275                1280                1285 gta gtc cct gtc gaa gat gaa ttc gat gac atc cct aat gaa act cca    4242
Val Val Pro Val Glu Asp Glu Phe Asp Asp Ile Pro Asn Glu Thr Pro
        1290                1295                1300 agc ata gta aag gca caa gaa gag caa tac gtc tcg ata atc aga aca    4290
Ser Ile Val Lys Ala Gln Glu Glu Gln Tyr Val Ser Ile Ile Arg Thr
    1305                1310                1315 acg tta ggg tac att cat acg aag ccc agg agt gcg atg gtc ttg gag    4338
Thr Leu Gly Tyr Ile His Thr Lys Pro Arg Ser Ala Met Val Leu Glu
1320                1325                1330 gac aag agc ccc ata gga aga tac atc gag gat gtg gaa gga cac gag    4386
Asp Lys Ser Pro Ile Gly Arg Tyr Ile Glu Asp Val Glu Gly His Glu
1335                1340                1345                1350 aag gaa cta tac tca ggg gtt gtc gag tta ctg tgc tgg aaa tcc gca    4434
Lys Glu Leu Tyr Ser Gly Val Val Glu Leu Leu Cys Trp Lys Ser Ala
            1355                1360                1365 ttg gag atc tta ggt aga aca aga gac act cat gca aca gtc ggg aca    4482
Leu Glu Ile Leu Gly Arg Thr Arg Asp Thr His Ala Thr Val Gly Thr
        1370                1375                1380 gaa gac cta cag ggg tgg ccc aga ata tac gcc tat aag gtc tca aga    4530
Glu Asp Leu Gln Gly Trp Pro Arg Ile Tyr Ala Tyr Lys Val Ser Arg
    1385                1390                1395 agg cac atc ata gga aag gtg acc tca ttc atc cta tac atc ctg gca    4578
Arg His Ile Ile Gly Lys Val Thr Ser Phe Ile Leu Tyr Ile Leu Ala
1400                1405                1410 gta caa ata gga gag ctc cct ctt cct tac agc atg gag aga gtt agc    4626
Val Gln Ile Gly Glu Leu Pro Leu Pro Tyr Ser Met Glu Arg Val Ser
1415                1420                1425                1430 cga cga gcg ata gat gta gtc tca cga gtc ggt ctt gag gga ttt tct    4674
Arg Arg Ala Ile Asp Val Val Ser Arg Val Gly Leu Glu Gly Phe Ser
            1435                1440                1445 gca gtt gcc tct ctt tgt cta ggg aga gat atc ccg atg gtg aat gat    4722
Ala Val Ala Ser Leu Cys Leu Gly Arg Asp Ile Pro Met Val Asn Asp
        1450                1455                1460 gtc gtg acc atc gta gat ggg ttt gct tat cca gag act gtg tcc gtc    4770
Val Val Thr Ile Val Asp Gly Phe Ala Tyr Pro Glu Thr Val Ser Val
    1465                1470                1475 tgc ctc aga tcc atc aag gca tct atc ctt atg acc ata ggc aag gtg    4818
Cys Leu Arg Ser Ile Lys Ala Ser Ile Leu Met Thr Ile Gly Lys Val
1480                1485                1490 atc aga gtg gat ggt ttc atg tcg aga agg agt gta tat ccg aca gag    4866
Ile Arg Val Asp Gly Phe Met Ser Arg Arg Ser Val Tyr Pro Thr Glu
1495                1500                1505                1510 tca atg acc tcg gac gat ttt ctg agg atc ttg gga ttc aag gct gtc    4914
Ser Met Thr Ser Asp Asp Phe Leu Arg Ile Leu Gly Phe Lys Ala Val
            1515                1520                1525 atc ttc tat ggg tgc aca aag atc cac gaa aag tgc caa cta aag gga    4962
Ile Phe Tyr Gly Cys Thr Lys Ile His Glu Lys Cys Gln Leu Lys Gly
```

-continued

```
                1530                1535                1540
ctt gac caa gtg acc tac gca gaa atg atg tgt cat cat aga tgt cta       5010
Leu Asp Gln Val Thr Tyr Ala Glu Met Met Cys His His Arg Cys Leu
        1545                1550                1555 gag aaa ctc cta tct tcc aac ctc cta acc cac atg acc atg gac aga       5058
Glu Lys Leu Leu Ser Ser Asn Leu Leu Thr His Met Thr Met Asp Arg
    1560                1565                1570 gcc atg aag tat cta ccc atc aaa atc acc aaa att ctc cct aag atc       5106
Ala Met Lys Tyr Leu Pro Ile Lys Ile Thr Lys Ile Leu Pro Lys Ile
1575                1580                1585                1590 tct tcc aca aga ccg aac aca att gcc gtg aca aga gaa gta gag act       5154
Ser Ser Thr Arg Pro Asn Thr Ile Ala Val Thr Arg Glu Val Glu Thr
            1595                1600                1605 gag aat cga gag ttt tcc gac acc ttc ccc att gat gag aga gtg aca       5202
Glu Asn Arg Glu Phe Ser Asp Thr Phe Pro Ile Asp Glu Arg Val Thr
        1610                1615                1620 tat cca gaa atg gat ctc aaa acc aat cag atg atc cag tat ccc aca       5250
Tyr Pro Glu Met Asp Leu Lys Thr Asn Gln Met Ile Gln Tyr Pro Thr
    1625                1630                1635 tca agc ata tac aaa tgg agt gac atc ctt ctc gga att gaa cat tac       5298
Ser Ser Ile Tyr Lys Trp Ser Asp Ile Leu Leu Gly Ile Glu His Tyr
        1640                1645                1650 gat cat gta gta gtc atg gga gat ggc act gga ggt aca tca atg gtt       5346
Asp His Val Val Val Met Gly Asp Gly Thr Gly Gly Thr Ser Met Val
1655                1660                1665                1670 gct gcg cac atg ttc ccg aac tcc acc ata tat cct atg gca ctc cta       5394
Ala Ala His Met Phe Pro Asn Ser Thr Ile Tyr Pro Met Ala Leu Leu
            1675                1680                1685 gaa agt aag aat ctg atc cct caa gac atg gaa tca ctt gcc cct cct       5442
Glu Ser Lys Asn Leu Ile Pro Gln Asp Met Glu Ser Leu Ala Pro Pro
        1690                1695                1700 atg tcc agg aag ctt aca aat gta gat tca tcc ctc ctg atc gat ctc       5490
Met Ser Arg Lys Leu Thr Asn Val Asp Ser Ser Leu Leu Ile Asp Leu
    1705                1710                1715 cct gat gac atc aga aag ccc aca ttc agg act agg atg cta gag aga       5538
Pro Asp Asp Ile Arg Lys Pro Thr Phe Arg Thr Arg Met Leu Glu Arg
        1720                1725                1730 gta tcg ctc atg cga gga aac att ctc atc atc tct gac att gag gga       5586
Val Ser Leu Met Arg Gly Asn Ile Leu Ile Ile Ser Asp Ile Glu Gly
1735                1740                1745                1750 act gga aca ttg ttc agg gac ata gta tcc aca tgt cta tac atg cct       5634
Thr Gly Thr Leu Phe Arg Asp Ile Val Ser Thr Cys Leu Tyr Met Pro
            1755                1760                1765 aca tca acg gat gtt ctc atg aaa aca cat cta gca gac ctc tgt gga       5682
Thr Ser Thr Asp Val Leu Met Lys Thr His Leu Ala Asp Leu Cys Gly
        1770                1775                1780 tca tat tac atg atg aag ggt gca gga agg att agg ctc aga ggt agt       5730
Ser Tyr Tyr Met Met Lys Gly Ala Gly Arg Ile Arg Leu Arg Gly Ser
    1785                1790                1795 cgg ttg gcg aac ctc aga tat gga gaa gta ttc gtc tca ttc aga gtc       5778
Arg Leu Ala Asn Leu Arg Tyr Gly Glu Val Phe Val Ser Phe Arg Val
        1800                1805                1810 acc gga ggg aac atc aga ccg aac aga aga ggg ctg ggg aac tgc att       5826
Thr Gly Gly Asn Ile Arg Pro Asn Arg Arg Gly Leu Gly Asn Cys Ile
1815                1820                1825                1830 cag gag gtg atg atc ggg ctc atg aat acc cag ata gag aca gca act       5874
Gln Glu Val Met Ile Gly Leu Met Asn Thr Gln Ile Glu Thr Ala Thr
            1835                1840                1845 gga atg ctc tcg cag atc gag tcc atg ttc ccc ttg gct gct gac atg       5922
```

```
                                                        -continued

Gly Met Leu Ser Gln Ile Glu Ser Met Phe Pro Leu Ala Ala Asp Met
        1850                1855                1860 agc atg aac ata gct atg atg aag atg gcc tca tgg gga gga tca ttc       5970
Ser Met Asn Ile Ala Met Met Lys Met Ala Ser Trp Gly Gly Ser Phe
        1865                1870                1875 tcg agg aag gtt ctg gga gaa gat ggg ctc aag ctg atg gga tat gtc       6018
Ser Arg Lys Val Leu Gly Glu Asp Gly Leu Lys Leu Met Gly Tyr Val
        1880                1885                1890 tac caa tac atc aat aca cac tac cat ttt gcc tca tcc tct tac agg       6066
Tyr Gln Tyr Ile Asn Thr His Tyr His Phe Ala Ser Ser Ser Tyr Arg
1895                1900                1905                1910 ccc gga gac aac aga aca gta aca cca agg aga aaa gag gat ctg acc       6114
Pro Gly Asp Asn Arg Thr Val Thr Pro Arg Arg Lys Glu Asp Leu Thr
            1915                1920                1925 aag ctc ctg tgc tcc att atg ttg ggg gtt tat gga gaa gat aca gag       6162
Lys Leu Leu Cys Ser Ile Met Leu Gly Val Tyr Gly Glu Asp Thr Glu
        1930                1935                1940 act att gag gaa gtg tcg aag tat acg ttg atc ggg agc aag aaa gga       6210
Thr Ile Glu Glu Val Ser Lys Tyr Thr Leu Ile Gly Ser Lys Lys Gly
        1945                1950                1955 gta cca gga aag agt tac ttc aag gtt ctg atg tgg aaa act ggg acc       6258
Val Pro Gly Lys Ser Tyr Phe Lys Val Leu Met Trp Lys Thr Gly Thr
    1960                1965                1970 aag aga gcc ttg gaa cac gat gag tac atg gtt ggg aga gca ata agg       6306
Lys Arg Ala Leu Glu His Asp Glu Tyr Met Val Gly Arg Ala Ile Arg
1975                1980                1985                1990 aac tac cgc acc aga att ctg gag gcc aag aaa ctg gat gga cct ata       6354
Asn Tyr Arg Thr Arg Ile Leu Glu Ala Lys Lys Leu Asp Gly Pro Ile
                1995                2000                2005 gga ttg cca ttc cat agt gga tcc cta agg aag att gcc acc tgg gga       6402
Gly Leu Pro Phe His Ser Gly Ser Leu Arg Lys Ile Ala Thr Trp Gly
            2010                2015                2020 tac aag att cca ata tct gca agc ggt gga tgg ata gac aat cac cta       6450
Tyr Lys Ile Pro Ile Ser Ala Ser Gly Gly Trp Ile Asp Asn His Leu
        2025                2030                2035 cag atc tga ggaccttgg aggatgaatg atgttgtgaa tagggagcac               6499
Gln Ile
    2040 gaatgtatga gcagacgatg aataagtccc aaatattaga aaaaacgaac ccagatagct     6559 cagtgactgt taattcctgc acaggctaat ggatcaagat atctagacaa catccaaagt     6619 cggaagtagg gaaatatcc gagcgtgtga acattggaaa aaatcaaaga cgaaccccc       6679 gggaataata aaacgttgga gtctcccagc ccgctaaagc aagttgagtt ctaacaaagc     6739 cgtgttagtc ggggtcttga tttttatgat tttgttgtgc tgtgtttgcg accg           6793

<210> SEQ ID NO 13
<211> LENGTH: 2040
<212> TYPE: PRT
<213> ORGANISM: Lettuce Big-vein Virus

<400> SEQUENCE: 13

Met Ser Leu Ala Ser Arg Met Thr Ser Val Gly Gly Ala Asp Asn Tyr
 1               5                  10                  15

Gly Glu Ser Asp Tyr Gly Trp Asp Glu Thr Val Leu Gly Asp Met His
            20                  25                  30

Leu Asn Ser Ala Ile Asn Leu Asp Leu Phe Lys Glu Phe Leu His Ile
        35                  40                  45

Asp Pro Pro Val Tyr Lys Val Lys Glu Asn His Arg Leu Thr Glu Glu
```

-continued

```
                50                  55                  60
Leu Arg Glu Leu Gln Ser Leu Ala Arg Lys Gly Ser Lys Ile Glu Ile
 65                  70                  75                  80

Gly Phe Gln Arg Leu Phe Ala Arg Met Phe Pro Arg Asp Gly Asn Leu
                 85                  90                  95

Ile Pro Met Asp Ser Thr Met Thr Arg Met Ile Met Lys Ile Ile Arg
            100                 105                 110

Asp Ser Gly Thr Lys Tyr Lys Leu Gly Ile Pro Leu Leu Gly Ile Ser
            115                 120                 125

Glu Glu Met Ile Lys Lys Gly Ala Met Val Pro Ser Asn Leu Val Tyr
        130                 135                 140

Ser Phe Asn Cys Phe Leu Asn Ile Ile Tyr Gly Arg Ser Glu Trp Ile
145                 150                 155                 160

Arg Ser Glu Gly Ile Ala Ile Arg Phe Lys Met Tyr Glu His Gly Arg
                165                 170                 175

Phe Ile Arg Arg Asp Leu Thr Ile Ser Glu Lys Glu Tyr Asn Phe Ile
            180                 185                 190

Val Gly Lys Glu Val Val Glu Ile Arg Ala Ser Arg Arg Lys Glu Arg
        195                 200                 205

Phe Ile Ala Asp Tyr Asn Ser Leu Leu Leu Leu Asp Val Ala Gly
        210                 215                 220

Gln Arg Ile Cys Ala His Leu Cys Ser Gln Leu Gly Glu Ile Ser Gly
225                 230                 235                 240

Val Pro Gly Ser Leu Ser Arg Tyr His Leu Glu Thr Leu Cys Thr Ala
                245                 250                 255

Gly Asp Arg Met Ile Glu Arg Cys Gly Asn Lys Ala Tyr Glu Val Leu
            260                 265                 270

Gly Met Tyr Glu Ala Leu Cys Val Gly Arg Leu Leu Glu Asn Asn Pro
        275                 280                 285

Asp Gly Ile Thr Asp His Thr Gln Phe Ser Ser Asn Cys Glu Glu Glu
        290                 295                 300

Leu Gln Glu Leu Ile Ala Gly Ser Val Glu Pro Ala Phe Met Lys Ser
305                 310                 315                 320

Gln Val Asp Leu Ile Lys Thr Thr Leu Glu Lys Met Lys Asn Gln Asp
                325                 330                 335

Ile Ser Asn Ala Phe Cys Leu Tyr Arg Val Trp Gly His Pro Thr Val
            340                 345                 350

Asp Ile Tyr Glu Gly Met Lys Lys Val His Thr Ile Gly Thr Lys Val
        355                 360                 365

Lys Val Ile Pro Pro Asn Leu Gly Thr Ile Met Val Cys Gln Phe Arg
        370                 375                 380

Lys Met Phe Met Ala Thr Phe Phe Lys Lys His His Arg Tyr Pro Pro
385                 390                 395                 400

Ile Thr Gly Thr Pro Gly Glu Tyr Leu Glu Arg Cys Leu Lys Asp Asn
                405                 410                 415

Val Ala Ile Arg Ile Glu His Leu Ala Tyr Asn Leu Arg Asp Phe Glu
            420                 425                 430

Phe Ile Arg Ile Gly Glu Thr Tyr Ser Val Pro Asp Thr Phe Asp Met
        435                 440                 445

Cys His Val Leu Asn Asp Lys Ala Val Ser Pro Asp Met Ser Glu Leu
        450                 455                 460

Leu Glu Ser Ile Lys Asn Gly Lys Gly Thr Ser Cys Gly Ala Lys Arg
465                 470                 475                 480
```

```
Arg Gly Ile Leu Arg Trp Met Glu Gly Asp Ser Leu Asn Cys Lys Ser
                485                 490                 495

Phe Leu Ser Asp Ile Asp Glu Lys Gly Leu Ser Glu Glu Asp Leu Leu
            500                 505                 510

Ile Gly Met Tyr Glu Lys Glu Arg Glu Ile Lys Val Ala Ala Arg Met
            515                 520             525

Tyr Ser Leu Met Thr Glu Arg Met Arg Tyr Tyr Phe Val Leu Thr Glu
        530                 535                 540

Gly Leu Ile Ala Asp Tyr Ile Leu Pro His Phe Pro Glu Ile Thr Met
545                 550                 555                 560

Lys Asp Ser Leu Asn Val Leu Leu Lys Lys Met Trp Glu Ser Gly Gly
                565                 570                 575

Gln Arg Ser Ile Gly Ser Met Asp Val Asn Ile Asn Ile Asp Phe Ser
                580                 585                 590

Lys Trp Asn Thr Asn Met Arg Glu Gly Pro Thr Ser Asp Thr Phe Arg
            595                 600                 605

Glu Met Asp Gly Ile Phe Gly Phe Lys Arg Leu Ile Ala Arg Thr His
        610                 615                 620

Glu Ile Phe Asn Ala Ser Leu Val Tyr Ser Ala Ser Gly Lys Tyr Leu
625                 630                 635                 640

Pro Thr Ile Glu Asp Gly Arg Ile Leu Asp Asp Pro Met Cys Tyr
                645                 650                 655

Arg Gly His Leu Gly Gly Phe Glu Gly Leu Arg Gln Lys Gly Trp Thr
                660                 665                 670

Val Ala Thr Val Cys Leu Leu Ala Tyr Leu Ser Glu Gln Asn Lys Ile
                675                 680                 685

Gln Met Lys Leu Met Gly Gln Gly Asp Asn Gln Ile Ile Arg Leu Arg
            690                 695                 700

Met Pro Thr Ser Tyr Trp Asp Ser Leu Arg Leu Thr Glu Glu Met Lys
705                 710                 715                 720

Lys Lys Glu Ala Arg Ile Leu Ser Asp Lys Phe Val His Glu Met Asp
                725                 730                 735

Ile Ile Phe Thr Gly Val Gly Leu Pro Ile Lys Val Arg Glu Thr Trp
                740                 745                 750

Lys Ser Thr Arg Leu Phe Met Tyr Gly Lys Val Met Leu Leu Asp Gly
            755                 760                 765

Arg Gln Leu Pro Gln Trp Tyr Lys Lys Thr Leu Arg Ser Tyr Ala Leu
            770                 775                 780

Ser Asn Glu Gly Thr Leu Thr Ile Ser Gly Val Ile Gly Thr Ile Ala
785                 790                 795                 800

Thr Asn Met Cys Ala Ala Gly Gly Ser Glu Val Pro Cys Val Met
                805                 810                 815

Tyr Leu Phe Phe Leu Leu Ala Glu Trp Ser Leu Glu Phe Met Phe
            820                 825                 830

Arg Tyr His Pro Phe Thr Arg Val Gly Ile Lys Asp Gly Ser Ser Met
            835                 840                 845

Glu Phe Arg Leu Asn Glu Lys Gly Gly Tyr Val His Lys Gln Thr Arg
        850                 855                 860

Lys Thr Asn Asn Leu Trp Leu Lys Ser Leu Leu Val Leu Val Pro Thr
865                 870                 875                 880

Ala Val Gly Gly Ser Val Thr Ile Pro Leu Thr Gly Phe Ile Met Arg
                885                 890                 895
```

```
Gly Phe Pro Asp Lys Ala Ser Glu Tyr Ala Trp Leu Lys Phe Leu
        900                 905                 910

Gly Ser Ser Lys Ser Pro Ile Gln Gly Phe Leu Lys Asn Phe Tyr Thr
        915                 920                 925

Phe Leu Pro Asn Asp Thr Val Glu Ala Asp Met Leu Val Gln Ser Pro
        930                 935                 940

Phe Ser Leu Thr His Lys Arg Pro Pro Thr Pro Gly Leu Gln Thr Lys
945                 950                 955                 960

Glu Asn Ile Arg Glu Trp Leu Leu Ser Thr Pro Arg Phe Gln Gln Asn
                965                 970                 975

Arg Phe Ile Arg Ser Met Gln Val Leu Leu Ser Gly Phe Asp Lys Lys
                980                 985                 990

Ser Val Cys Arg Glu Leu Leu Thr Glu Arg Met Asn Pro Leu Ile Ser
        995                 1000                1005

His Glu Val Tyr Glu Thr Phe Gly His Val Tyr Cys Glu Gly Ile Val
        1010                1015                1020

Ala Arg Val Glu Asn Thr Arg Thr Ile Arg Thr Leu His Leu Ser Arg
1025                1030                1035                1040

Glu Asp Arg Lys Pro Ile Val Ala Lys Leu Met Thr Asp Glu Met Ala
                1045                1050                1055

Tyr Ile Ala Tyr Met Trp Trp Arg Gly Asn Thr Lys Gly Glu Val Phe
                1060                1065                1070

Glu Glu Cys Ala Thr Lys Gln Ala Arg Lys Gly Arg Asn Val Gly Trp
                1075                1080                1085

Lys Arg Glu Ile Val Gly Ile Thr Thr Pro His Pro Leu Glu Val Leu
                1090                1095                1100

Phe Gln Ser Val Cys Arg Pro Gly Asp Gln Cys Gln Arg Ser Asp Asp
1105                1110                1115                1120

Tyr Ile Thr Ser Lys Leu Val Asp Asp Gly Lys Phe Pro Pro Phe Leu
                1125                1130                1135

Gly Ser Lys Ile Lys Asn Lys Val Tyr Ser Leu Gln Asp Glu Glu Ala
                1140                1145                1150

Arg Arg Glu Pro Leu Ile Lys Thr Gly Ala Arg Leu Ala Arg Gln Phe
                1155                1160                1165

Asn Trp Ile Gly Met Gly Glu Asn Met Arg Gly Leu Val Leu Lys Asn
        1170                1175                1180

Val Gly Ser Ile Cys Asp Val Ser Val Phe Asp Lys Phe Val Asp Asp
1185                1190                1195                1200

Asp Pro Ser Asp Asn Leu Tyr Thr Gly Ser Leu Met His Arg Phe Thr
                1205                1210                1215

Pro Ser Ser Val Ser Glu Gly Cys Phe Ile Asn Tyr Ala Pro Gln Val
        1220                1225                1230

Gly His Lys Val Phe Met Ser Ser Asp Thr Leu Pro Ser Leu Ser Arg
        1235                1240                1245

Gly Gln Thr Asn Tyr Thr Phe His Phe Gln Ala Met Tyr Cys Phe Leu
        1250                1255                1260

Gln Tyr Ser Ile Ser Lys Ser Gly Asn Glu Gly Ser Tyr His His His
1265                1270                1275                1280

Ile Met Cys Gln Asp Cys Val Val Pro Val Glu Asp Glu Phe Asp Asp
                1285                1290                1295

Ile Pro Asn Glu Thr Pro Ser Ile Val Lys Ala Gln Glu Glu Gln Tyr
                1300                1305                1310

Val Ser Ile Ile Arg Thr Thr Leu Gly Tyr Ile His Thr Lys Pro Arg
```

-continued

Ser Ala Met Val Leu Glu Asp Lys Ser Pro Ile Gly Arg Tyr Ile Glu
1315                1320                1325

Asp Val Glu Gly His Glu Lys Glu Leu Tyr Ser Gly Val Val Glu Leu
1330                1335                1340

Leu Cys Trp Lys Ser Ala Leu Glu Ile Leu Gly Arg Thr Arg Asp Thr
1345                1350                1355                1360

His Ala Thr Val Gly Thr Glu Asp Leu Gln Gly Trp Pro Arg Ile Tyr
1365                1370                1375

Ala Tyr Lys Val Ser Arg Arg His Ile Ile Gly Lys Val Thr Ser Phe
1380                1385                1390

Ile Leu Tyr Ile Leu Ala Val Gln Ile Gly Glu Leu Pro Leu Pro Tyr
1395                1400                1405

Ser Met Glu Arg Val Ser Arg Arg Ala Ile Asp Val Val Ser Arg Val
1410                1415                1420

Gly Leu Glu Gly Phe Ser Ala Val Ala Ser Leu Cys Leu Gly Arg Asp
1425                1430                1435                1440

Ile Pro Met Val Asn Asp Val Val Thr Ile Val Asp Gly Phe Ala Tyr
1445                1450                1455

Pro Glu Thr Val Ser Val Cys Leu Arg Ser Ile Lys Ala Ser Ile Leu
1460                1465                1470

Met Thr Ile Gly Lys Val Ile Arg Val Asp Gly Phe Met Ser Arg Arg
1475                1480                1485

Ser Val Tyr Pro Thr Glu Ser Met Thr Ser Asp Asp Phe Leu Arg Ile
1490                1495                1500

Leu Gly Phe Lys Ala Val Ile Phe Tyr Gly Cys Thr Lys Ile His Glu
1505                1510                1515                1520

Lys Cys Gln Leu Lys Gly Leu Asp Gln Val Thr Tyr Ala Glu Met Met
1525                1530                1535

Cys His His Arg Cys Leu Glu Lys Leu Leu Ser Ser Asn Leu Leu Thr
1540                1545                1550

His Met Thr Met Asp Arg Ala Met Lys Tyr Leu Pro Ile Lys Ile Thr
1555                1560                1565

Lys Ile Leu Pro Lys Ile Ser Ser Thr Arg Pro Asn Thr Ile Ala Val
1570                1575                1580

Thr Arg Glu Val Glu Thr Glu Asn Arg Glu Phe Ser Asp Thr Phe Pro
1585                1590                1595                1600

Ile Asp Glu Arg Val Thr Tyr Pro Glu Met Asp Leu Lys Thr Asn Gln
1605                1610                1615

Met Ile Gln Tyr Pro Thr Ser Ser Ile Tyr Lys Trp Ser Asp Ile Leu
1620                1625                1630

Leu Gly Ile Glu His Tyr Asp His Val Val Val Met Gly Asp Gly Thr
1635                1640                1645

Gly Gly Thr Ser Met Val Ala Ala His Met Phe Pro Asn Ser Thr Ile
1650                1655                1660                1665

Tyr Pro Met Ala Leu Leu Glu Ser Lys Asn Leu Ile Pro Gln Asp Met
1670                1675                1680

Glu Ser Leu Ala Pro Pro Met Ser Arg Lys Leu Thr Asn Val Asp Ser
1685                1690                1695

Ser Leu Leu Ile Asp Leu Pro Asp Asp Ile Arg Lys Pro Thr Phe Arg
1700                1705                1710

Thr Arg Met Leu Glu Arg Val Ser Leu Met Arg Gly Asn Ile Leu Ile
1715                1720                1725

-continued

```
Ile Ser Asp Ile Glu Gly Thr Gly Thr Leu Phe Arg Asp Ile Val Ser
1745                1750                1755                1760

Thr Cys Leu Tyr Met Pro Thr Ser Thr Asp Val Leu Met Lys Thr His
            1765                1770                1775

Leu Ala Asp Leu Cys Gly Ser Tyr Tyr Met Met Lys Gly Ala Gly Arg
        1780                1785                1790

Ile Arg Leu Arg Gly Ser Arg Leu Ala Asn Leu Arg Tyr Gly Glu Val
    1795                1800                1805

Phe Val Ser Phe Arg Val Thr Gly Gly Asn Ile Arg Pro Asn Arg Arg
1810                1815                1820

Gly Leu Gly Asn Cys Ile Gln Glu Val Met Ile Gly Leu Met Asn Thr
1825                1830                1835                1840

Gln Ile Glu Thr Ala Thr Gly Met Leu Ser Gln Ile Glu Ser Met Phe
            1845                1850                1855

Pro Leu Ala Ala Asp Met Ser Met Asn Ile Ala Met Met Lys Met Ala
        1860                1865                1870

Ser Trp Gly Gly Ser Phe Ser Arg Lys Val Leu Gly Glu Asp Gly Leu
    1875                1880                1885

Lys Leu Met Gly Tyr Val Tyr Gln Tyr Ile Asn Thr His Tyr His Phe
1890                1895                1900

Ala Ser Ser Ser Tyr Arg Pro Gly Asp Asn Arg Thr Val Thr Pro Arg
1905                1910                1915                1920

Arg Lys Glu Asp Leu Thr Lys Leu Leu Cys Ser Ile Met Leu Gly Val
            1925                1930                1935

Tyr Gly Glu Asp Thr Glu Thr Ile Glu Glu Val Ser Lys Tyr Thr Leu
        1940                1945                1950

Ile Gly Ser Lys Lys Gly Val Pro Gly Lys Ser Tyr Phe Lys Val Leu
    1955                1960                1965

Met Trp Lys Thr Gly Thr Lys Arg Ala Leu Glu His Asp Glu Tyr Met
1970                1975                1980

Val Gly Arg Ala Ile Arg Asn Tyr Arg Thr Arg Ile Leu Glu Ala Lys
1985                1990                1995                2000

Lys Leu Asp Gly Pro Ile Gly Leu Pro Phe His Ser Gly Ser Leu Arg
            2005                2010                2015

Lys Ile Ala Thr Trp Gly Tyr Lys Ile Pro Ile Ser Ala Ser Gly Gly
        2020                2025                2030

Trp Ile Asp Asn His Leu Gln Ile
        2035                2040

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: (21)..(26)
<223> OTHER INFORMATION: "n" indicates a or g or c or t.

<400> SEQUENCE: 14
gccggagctc tgcagaattc nnnnnn                                          26

<210> SEQ ID NO 15
<211> LENGTH: 20
<212> TYPE: DNA
```

-continued

```
<213> ORGANISM: Artificial Sequence
<220> FEATURE:
<223> OTHER INFORMATION: Description of Artificial Sequence:an
      artificially synthesized primer sequence

<400> SEQUENCE: 15
gccggagctc tgcagaattc                                              20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 16
agctctgaac aacgacatg                                               19
```

NUCLEIC ACIDS ENCODING LETTUCE BIG-VEIN VIRAL PROTEINS AND UTILIZATION THEREOF

TECHNICAL FIELD

The present invention relates to nucleic acids encoding lettuce big-vein viral proteins, proteins encoded by the nucleic acids, and their production and use.

BACKGROUND ART

Lettuce big-vein virus (LBVV) is a virus belonging to Varicosavirus, is composed of two RNAs (7.0 kb and 6.5 kb RNA), and retains a coat protein of 48 kDa. LBVV is a soil-borne virus that is spread in the soil by *Olpidum brassicae*, and occurs in the United States, Australia, New Zealand, Japan and Europe. Since this virus infects lettuce and remarkably lowers its quality and yield, it is a serious problem in lettuce production.

Unfortunately, there has not yet been reported the existence of a gene that makes lettuce resistant to this virus. Although several cultivars such as Entree, Sea Green and Pacific are commercially available as LBVV-resistant cultivars, their resistance is low. Thus, there has not yet been found a radical solution to disease damage caused by LBVV.

Elucidation of the virus genetic information is an important step in preventing disease damage caused by the virus. However, isolation and purification of LBVV are extremely difficult for reasons such as the instability of the viral particles, tendency for viral particles to readily aggregate with each other, and extremely low concentration of the virus in plants. Although, so far, two successful examples of purification of the virus have been reported (S. Kuwata et al., (1983), Annals of the Phytopathological Society of Japan, 49, 246-251; and, H. J. Vetten et al. (1987), Journal of Phytopathology, 120, 53-59), the reproducibility is low and the purified amounts are extremely low. Consequently, as to LBVV, no genetic information has been elucidated at all.

DISCLOSURE OF THE INVENTION

The present invention has been achieved in consideration of the above circumstances, and objectives of the present invention are to isolate lettuce big-vein viral (LBVV) proteins and nucleic acids that encode the proteins and to elucidate the structure thereof. In addition, another objective of the present invention is to endow lettuce with resistance to LBVV through expression of the nucleic acid or its antisense nucleic acid in lettuce. Moreover, still another objective of the present invention is to provide a method of diagnosing infection with LBVV by detecting the nucleic acid or a protein encoded by the nucleic acid.

LBVV is an RNA virus, and it is likely that, if a DNA encoding a protein of the virus or its antisense DNA is expressed in a plant, the production and function of LBVV proteins can be inhibited at the transcription level or translation level (P. F. Tennant et al., (1994), Phytopathology, 84, 1359-1366; C. C. Huntley & T. C. Hall, (1993), Virology, 192, 290-297; D. C. Baulcombe, (1996), The Plant Cell, 8, 1833-1844).

The present inventors focused on this idea, and isolated the genes encoding LBVV proteins in order to produce lettuce resistant to LBVV.

Specifically, the present inventors first obtained highly purified LBVV, and then applied this to SDS-polyacrylamide gel electrophoresis to detect the coat protein that constitutes the virus. The detected coat protein was purified and then decomposed into peptides, followed by determination of the partial amino acid sequences of the peptides by the Edman's method. Moreover, an RNA encoding the coat protein of LBVV was cloned by polymerase chain reaction (PCR) using primers designed on the basis of information from the determined amino acid sequences, followed by determination of its nucleotide sequence.

Next, in order to determine the gene that encodes the full-length coat protein of LBVV, RNAs were prepared from purified virus and from leaf infected with the virus that had exhibited obvious symptoms of infection, and 3'RACE and 5'RACE were carried out using these RNA molecules. As a result, the present inventors have succeeded not only in isolating the RNA molecule that encodes LBVV coat protein, but also in determining its primary structure. Moreover, by genome walking method, the present inventors have succeeded in isolating RNA molecules encoding four other non-structural proteins of LBVV and in determining their primary structures as well.

Similarly, the present inventors also succeeded in isolating an RNA molecule that encodes a polymerase protein from highly purified LBVV.

The isolated RNA molecule or its antisense molecule is able to endow lettuce plants with resistance to LBVV by its expression, and thereby, it is possible to improve lettuce productivity. In addition, genetic diagnosis of LBVV can also be carried out by designing and using a primer specific to LBVV based on sequence information of the isolated RNA molecules. Furthermore, the antisera that bind to LBVV proteins can be produced based on the resulting sequence information, and these can be used for serological diagnosis of LBVV.

The present invention was completed on the basis of the above findings, and provides LBVV proteins, nucleic acids encoding the proteins, and their production and use.

More specifically, the present invention provides the following:

(1) a nucleic acid encoding a protein of lettuce big-vein virus, said nucleic acid selected from the group consisting of:
  (a) a nucleic acid encoding a protein comprising the amino acid sequence of any one of SEQ ID NOs: 2 through 6 and SEQ ID NO: 13; and
  (b) the nucleic acid of (a) comprising the coding region of the nucleotide sequence of SEQ ID NO: 1 or 12;

(2) the nucleic acid according to (1), wherein the nucleic acid is an RNA;

(3) the nucleic acid according to (1), wherein the nucleic acid is a DNA;

(4) a DNA encoding a sense RNA complementary to a complementary strand of the nucleic acid according to (2);

(5) a DNA encoding an antisense RNA complementary to the nucleic acid according to (2);

(6) a DNA encoding an RNA having ribozyme activity that specifically cleaves the nucleic acid according to (2);

(7) a vector comprising the nucleic acid according to (3);

(8) a transformed cell comprising the nucleic acid according to (3), or the vector according to (7);

(9) a protein encoded by the nucleic acid according to (1);

(10) an antibody that binds to the protein of (9);

(11) a method of producing the protein according to (9) wherein said method comprises the steps of:
  (a) culturing the transformed cell of (8); and
  (b) recovering an expressed protein from said transformed cell or its culture supernatant;

(12) a vector comprising the DNA according to any one of (4) through (6);

(13) a transformed lettuce cell that comprises the nucleic acid according to (1), the DNA according to any one of (4) through (6), or the vector according to (7) or (12);

(14) a transformed lettuce plant comprising the transformed lettuce cell according to (13);

(15) a transformed lettuce plant that is a progeny or a clone of the transformed lettuce plant according to (14);

(16) a propagation material of the transformed lettuce plant according to (14) or (15); and

(17) a method of diagnosing infection caused by the lettuce big-vein virus wherein said method comprises the step of:

detecting the nucleic acid of (1), or detecting the protein of (9) in lettuce cells; in *Olpidum brassicae*, a fungal vector of lettuce big-vein virus; or in soil comprising the fungal vector.

The present invention provides LBVV proteins and nucleic acids encoding the proteins. The nucleotide sequence of cDNA that encodes LBVV proteins isolated by the present inventors and that is included in the present invention is shown in SEQ ID NO: 1, and the amino acid sequences of the proteins encoded by the cDNA are shown in SEQ ID NOs: 2 through 6. The isolated cDNA is a 6078 nucleotides sequence and encodes five proteins. Protein 1 (coat protein: Example 1) has a translation initiation site at nucleotide 209 and encodes 397 amino acids (the isolated clone was named "LBVV-cp"/SEQ ID NO: 2); protein 2 (Example 3) has a translation initiation site at nucleotide 1492 and encodes 333 amino acids (SEQ ID NO: 3); protein 3 (Example 3) has a translation initiation site at nucleotide 2616 and encodes 290 amino acids (SEQ ID NO: 4); protein 4 (Example 3) has a translation initiation site at nucleotide 3842 and encodes 164 amino acids (SEQ ID NO: 5); and protein 5 (Example 3) has a translation initiation site at nucleotide 4529 and encodes 368 amino acids (SEQ ID NO: 6).

In addition, the nucleotide sequence of cDNA (Example 4) that encodes a polymerase of LBVV isolated by the present inventors and that is also included in the present invention is shown in SEQ ID NO: 12, and the amino acid sequence of the protein encoded by the cDNA is shown in SEQ ID NO: 13 (the isolated clone was named "LBVV-L"). The isolated cDNA is a 6793 nucleotides sequence, has a translation initiation site at nucleotide 337, and encodes 2040 amino acids.

Moreover, the present inventors have revealed that LBVV is a negative-strand RNA virus that contains more positive-strands in its viral particles than usual.

This is the first example of demonstrating the genes and protein primary structures of LBVV.

Nucleic acids encoding LBVV-cp protein (LBVV protein 1) LBVV proteins 2 to 5, or LBVV-L protein according to the present invention include a DNA and an RNA. The DNA includes a cDNA and a chemically synthesized DNA, and the RNA includes a viral genomic RNA, mRNA, and synthetic RNA. A nucleic acid of the present invention can be prepared using conventional means by a person with ordinary skill in the art. Specifically, a first strand DNA can be synthesized by carrying out a reverse transcription reaction using, as a template, (1) an RNA prepared by de-proteinizing purified virus by a method such as the SDS-phenol method or (2) the total nucleic acids extracted from a virus-infected leaf by the CTAB method and so on and using a primer designed from the sequence of a nucleic acid of the present invention or a random primer. From the first strand DNA prepared by this method, a second strand DNA can be synthesized according to the method of Gubler & Hoffman (U. Gubler and B. J. Hoffman, (1983), Gene 25, 263-269), and the nucleic acid of the present invention can be cloned in various commercially available plasmids or phagemid vectors. Alternatively, a DNA encoding an RNA of the virus can be amplified by polymerase chain reaction using a primer designed from the sequence of a nucleic acid of the present invention and using the first strand DNA as a template, and the nucleic acid of the present invention can be cloned by TA cloning using the pGEM®-T vector and so on or by cloning in various commercially available plasmid vectors by adding a restriction enzyme site to the primer.

A nucleic acid of the present invention can also be used for the preparation of recombinant protein and for the production of lettuce resistant to LBVV.

A recombinant protein is usually prepared by inserting a DNA encoding a protein of the present invention into an appropriate expression vector, introducing the vector into an appropriate cell, culturing the transformed cells, allowing the cells to express the recombinant protein, and purifying the expressed protein. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited so long as the cell is suitable for expressing the recombinant protein. It is possible to utilize yeasts or various animal, plant, or insect cells by change the expression vector, besides the above described *E. coli*. A vector can be introduced into a host cell by a variety of methods known to one skilled in the art. For example, a transformation method using calcium ions (Mandel, M. and Higa, A. (1970) Journal of Molecular Biology, 53, 158-162, Hanahan, D. (1983) Journal of Molecular Biology, 166, 557-580) can be used to introduce a vector into *E. coli*. A recombinant protein expressed in host cells can be purified and recovered from the host cells or the culture supernatant thereof by known methods. When a recombinant protein is expressed as a fusion protein with maltose binding protein or other partners, the recombinant protein can be easily purified by affinity chromatography.

The resulting protein can be used to prepare an antibody that binds to the protein. For example, a polyclonal antibody can be prepared by immunizing immune animals, such as rabbits, with a purified protein of the present invention or its portion, collecting blood after a certain period, and removing clots. A monoclonal antibody can be prepared by fusing myeloma cells with the antibody-forming cells of animals immunized with the above protein or its portion, isolating a monoclonal cell expressing a desired antibody (hybridoma), and recovering the antibody from the cell. The obtained antibody can be utilized to purify or detect a protein of the present invention. The antibody of the present invention includes antiserum, polyclonal antibody, monoclonal antibody, and fragment thereof.

In the case of producing LBVV-resistant lettuce, a DNA that represses the production and function of LBVV proteins should be introduced into lettuce cells, and the resulting transformed lettuce cells should be regenerated.

A DNA encoding an RNA that hybridizes with either strand (sense strand or complementary strand) of an RNA encoding LBVV proteins can be used as the DNA that represses the production and function of the LBVV proteins.

Examples of a DNA encoding an RNA that hybridizes with viral genomic sense strand and with mRNAs include a DNA that encodes an antisense RNA that is complementary to the transcription product of a DNA encoding the protein described in any one of SEQ ID NOs: 2 through 6 and SEQ ID NO: 13 isolated by the present inventors (preferably, a DNA comprising a coding region of the nucleotide sequence described in SEQ ID NO: 1 or SEQ ID NO: 12). Herein, the term "complementary" also means not completely complementary so long as the production of LBVV proteins can be effectively inhibited. The transcribed RNA has preferably 90% or more complementarity and most preferably 95% or more complementarity to the RNA encoding the target LBVV protein. Herein, the term "complementarity" refers to the percentage of the number of nucleotides that form complementary base pairs, to the total number of base pairs in a region where the two sequences correspond to each other, in the case that the sequences are aligned so that the number of complementary base pairs may be maximized.

The DNA that encodes a sense RNA complementary to a complementary strand of RNA encoding the protein described in any one of SEQ ID NOs: 2 through 6 and SEQ ID NO: 13 isolated by the present inventors (preferably, an RNA comprising a coding region of the nucleotide sequence described in SEQ ID NO: 1 or SEQ ID NO: 12) can be used as a DNA encoding an RNA that hybridizes with a complementary strand of viral genomic RNA. Herein, the term "complementary" also means not completely complementary so long as the production of LBVV proteins can be effectively inhibited. The transcribed sense RNA has preferably 90% or more complementarity and most preferably 95% or more complementarity to the RNA (complementary strand) encoding the target LBVV protein.

In order to effectively inhibit the expression of the target gene, the above described antisense and sense DNAs should be at least 15 nucleotides long, more preferably at least 100 nucleotides long, and still more preferably at least 500 nucleotides long. These DNAs are generally shorter than 5 kb, and preferably shorter than 2.5 kb.

In addition, it is likely that a DNA encoding a ribozyme that cleaves at least one of the strands of an RNA that encodes LBVV proteins can be used as a DNA that represses the production of the LBVV proteins.

A ribozyme is an RNA molecule that has catalytic activities. There are many ribozymes having various activities. Research on the ribozymes as RNA cleaving enzymes has enabled the design of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka (1990) Tanpakushitsu Kakusan Kohso (Nucleic acid, Protein, and Enzyme) 35: 2191-2200).

The self-cleavage domain of a hammerhead type ribozyme cleaves at the 3' side of C15 of the sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (M. Koizumi et al. (1988) FEBS Letters, 228: 228-230). If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (M. Koizumi et al. (1988) FEBS Letters, 239: 285; Makoto Koizumi and Eiko Ohtsuka (1990) Tanpakushitsu Kakusan Kohso (Protein, Nucleic acid, and Enzyme), 35: 2191-2200; M. Koizumi et al. (1989) Nucleic Acids Research, 17: 7059-7071). For example, in LBVV-cp gene, LBVV protein 2 to 5 genes, or LBVV-L gene (SEQ ID NO: 1 or 12), there are a plurality of sites that can be used as the ribozyme target.

The hairpin type ribozyme is also useful in the present invention. A hairpin type ribozyme can be found, for example, in the minus strand of the satellite RNA of Tobacco ringspot virus (J. M. Buzayan, Nature 323: 349-353 (1986)). This ribozyme has also been shown to target-specifically cleave RNA (Y. Kikuchi and N. Sasaki (1992) Nucleic Acids Research, 19: 6751-6775; Yo Kikuchi (1992) Kagaku To Seibutsu (Chemistry and Biology) 30: 112-118).

The ribozyme designed to cleave the target is fused with a promoter, such as the cauliflower mosaic virus 35S promoter, and with a transcription termination sequence, so that it will be transcribed in plant cells. However, if extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (K. Taira et al. (1990) Protein Eng. 3: 733-738; A. M. Dzaianott and J. J. Bujarski (1989) Proc. Natl. Acad. Sci. USA 86: 4823-4827; C. A. Grosshands and R. T. Cech (1991) Nucleic Acids Research, 19: 3875-3880; K. Taira et al. (1991) Nucleic Acid Research, 19: 5125-5130). Multiple sites within the target gene can be cleaved by arranging these structural units in tandem to achieve greater effects (N. Yuyama et al., Biochem. Biophys. Res. Commun. 186: 1271-1279 (1992)). By using such ribozymes, it is possible to specifically cleave the transcription products of the target gene in the present invention, thereby repressing the expression of the gene.

Vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter); and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus.

A vector can be introduced into lettuce cells by known methods, such as the polyethylene glycol method, polycation method, electroporation, Agrobacterium mediated transfer, and particle bombardment. For example, the method described in the literature (S. Z. Pang et al., (1996), The Plant Journal, 9, 899-909) is a preferable one.

Regeneration of a lettuce plant from transformed lettuce cells can be carried out by methods known to a person with ordinary skill in the art according to the type of lettuce cells. Examples of preferable regeneration methods are described in the literature (S. Enomoto, et al., (1990), Plant Cell Reports, 9, 6-9).

Once a transformed lettuce plant in which the DNA of the present invention is introduced into the genome is obtained, it is possible to gain progenies from that plant by sexual propagation. Alternatively, plants can be mass-produced from propagation materials (for example, seeds, tubs, callus, protoplast, and so on) obtained from the plant, or progenies or clones thereof. The present invention includes plant cells transformed with the DNA of the present invention; plants including these cells; progenies and clones of the plants; and propagation materials of the plants and their progenies and clones.

In addition, the present invention provides a method of diagnosing infection with LBVV. One embodiment of the diagnostic method of the present invention comprises detecting, using a primer or probe, a LBVV RNA or an RNA encoding the viral protein. Nucleic acid comprising at least 15 nucleotides homologous or complementary to a DNA encoding the LBVV protein described in any one of SEQ ID NOs: 2 through 6 and 13 can be used for the probe or primer. The nucleic acid is preferably nucleic acid that specifically hybridizes with a DNA encoding the LBVV protein described in any one of SEQ ID NOs: 2 through 6 and 13.

The primer or probe may be labeled as necessary. Examples of labels include a radioactive label.

In this diagnosis, for example, a test sample is prepared from lettuce suspected of being infected with lettuce big-vein virus, Olpidum harboring the virus, or soil containing the virus, and PCR using the above primer or northern blotting using the above probe is carried out on the sample.

Another mode of the diagnostic method of the present invention is a method characterized by detecting LBVV proteins using antibody. Antibody used in this diagnosis can be prepared, for example, by synthesizing peptide using the antigenic region estimated from the resulting amino acid sequences (any of SEQ ID NOs: 2 through 6 and 13), by binding the peptide to a carrier protein such as KLH or BSA, and by immunizing rabbits with this. In addition, the antibody can also be produced by tagging LBVV proteins with histidine using the QIAexpress Type IV Kit (QIAGEN), by expressing the tagged protein in *E. coli*, and by immunizing rabbits with the resulting protein. The antibody may be labeled as necessary. Examples of labels include an enzyme label. In addition, instead of directly labeling the antibody itself, the antibody may be labeled via a substance such as protein A that binds to the antibody, followed by detection of the target protein.

In this diagnosis, a test sample is prepared from, for example, lettuce suspected of being infected with lettuce big-vein virus, Olpidum harboring the virus, or soil containing the virus, and then, ELISA or western blotting is carried out on the sample using the above antibody.

BEST MODE FOR CARRYING OUT THE INVENTION

The present invention is specifically illustrated below with reference to the examples, but is not construed as being limited thereto.

EXAMPLE 1

Cloning of Coat Protein Gene of Lettuce Big-vein Virus (LBVV)

Contaminated soil was sampled from a lettuce (cultivar: Cisco) field in Kagawa Prefecture, Japan that exhibited characteristic big-vein symptoms in 1997. The virus was maintained in resting spores in dry soil kept in the laboratory. Cisco, a cultivar of lettuce, was used for virus purification, and the virus was inoculated by regular transfer in soil.

Virus purification was carried out by modifying the method of Kuwata et al. (S. Kuwata, et al., (1983), Annals of the Phytopathological Society of Japan, 49, 246-251). The First step of sedimenting virions by low-speed centrifugation was omitted. The virus fraction was obtained by treating with 1% Triton-X and 1% Briji-35, followed by $C_2SO_4$ density gradient centrifugation. When the purified virus obtained by this purification method was subjected to SDS-polyacrylamide electrophoresis, only a single 48 kDa band was detected. In addition, since only clusters of LBVV particles were observed by electron microscopy while other impurities were not observed, the resulting virus was presumed to have considerably high purity.

After treatment of the purified virus with Proteinase K-SDS, extraction of viral nucleic acid was carried out by phenol/chloroform and ethanol precipitation. The purified viral nucleic acid was used for synthesis of first strand cDNA after denaturing with dimethylsulfoxide. Poly(A)+RNA was isolated from the virus-infected lettuce leaf that exhibited obvious big-vein symptoms by using the Dynabeads® mRNA DIRECT™ Kit (Dynal®). Synthesis of first strand cDNA was performed by carrying out a reverse transcription reaction with SUPERSCRIPT™ II Rnase H⁻ Reverse Transcriptase (Gibco BRL) using a random primer or an Oligo-dT-Bam HI primer.

Determination of the internal amino acid sequences of LBVV coat protein was carried out in the manner described below. After purified LBVV was subjected to 12.5% SDS-polyacrylamide electrophoresis, the polypeptides were transferred to a nitrocellulose membrane and the band of interest was cut out followed by carboxymethylation, and treatment with lysyl endopeptidase. After the treatment, 38 peptide fragments of the LBVV coat protein were obtained by reverse phase HPLC, and the amino acid sequences of several internal peptide fragments were determined.

5LB111 primer (GARWSITGGGAYGAYGARWSIAC/ SEQ ID NO: 7) and 3LB171 primer (GCRTCDATRTART-CIACICCIGG/SEQ ID NO: 8) were designed based on ESWDDESTIAMP (SEQ ID NO: 17) and NLEVPGVDYIDA (SEQ ID NO: 18) of the resulting amino acid sequences. PCR was carried out using these primers and Takara Taq (Takara), a 274 bp PCR product was obtained. The resulting PCR product was cloned using pGEM®-T Easy Vector Systems (Promega) and its nucleotide sequence was determined.

In order to determine the full-length coat protein gene of LBVV, 3'RACE or 5'RACE were aimed using an RNA from the purified virus or a Poly(A)+RNA from the LBVV-infected leaf. In the case of 3'RACE, 891-bp PCR product was obtained using a Poly(A)+RNA from the LBVV-infected leaf, and using Olido-dT-Bam HI primer and 5LB171 primer (AAYYTIGARGTICCIGGIGTIGA/SEQ ID NO: 9). In the case of 5'RACE, a 760-bp PCR product was obtained with the 5'RACE System for Rapid Amplification of cDNA Ends, Version 2.0 (Gibco BRL) using an RNA from purified virus or a Poly(A)+RNA from the LBVV-infected leaf, and using 3LB5R4 primer (GTTTTTGACCCTGATAG/SEQ ID NO: 10) and 3LB5R5 primer (GTCGACTCTAGACACT-TGTTGTTTGTCGTG/SEQ ID NO: 11). The resulting PCR products were cloned using pGEM®-T Easy Vector Systems (Promega), and the nucleotide sequences were determined for at least six clones or more. In addition, the 500- to 700-bp PCR products from the region in the vicinity of the coat protein gene were recloned using mutually overlapping virus-specific primers. At least three clones were sequenced from each region, and the nucleotide sequence of coat protein gene was confirmed.

A 1425 nucleotides sequence was determined using the above method. This gene had a translation initiation site at nucleotide 209, and encoded 397 amino acids (see SEQ ID NO: 1).

EXAMPLE 2

Production of Transformed Lettuce (1) Sterilization and Culturing of Lettuce Seeds Lettuce seeds were immersed for several seconds in 70% ethanol followed by treating for 15 minutes in a sterilization solution (10% sodium hypochlorite, 0.05% Tween-20). Next, the seeds were rinsed with sterilized water, seeded on Hyponex agar medium (prepared by dissolving 3.0 g of Hyponex powder, 10.0 g of sucrose and 8.0 g of agar in one liter of distilled water and then adjusting the pH to 5.8 with 1 N NaOH) in a plant box, and grown for about 2 weeks under the light condition at 25 to 28° C. until the true leaf reached about 5 cm.

(2) Culturing and Inoculation of Agrobacterium

Agrobacterium was inoculated into YEB liquid medium (prepared by dissolving 1.0 g of yeast extract, 5.0 g of beef extract, 5.0 g of peptone, 5.0 g of sucrose and 0.5 g of $MgSO_4$ $7H_2O$ in one liter of distilled water and then adjusting the pH to 7.0 with 1 N NaOH) comprising 250 µg/ml streptomycin, 5 µg/ml rifampicin and 50 µg/ml kanamycin, and then cultured with shaking overnight at 28° C. The Agrobacterium culture liquid was then sub-cultured to fresh YEB medium (comprising the above-mentioned antibiotics) and additionally cultured with shaking for one day at 28° C.

The young lettuce plants in which the true leaf had grown to about 5 cm were transferred to plastic Petri dishes, the true leaf was cut into pieces measuring about 5 mm, and the pieces of the leafs were immersed for 1 minute in Agrobacterium culture liquid diluted ten-fold. Next, the pieces were arranged on Murashige & Skoog medium (MS medium) (pH 5.8) comprising 3% sucrose, 0.5 ppm benzyladenine phosphate (BAP), 0.1 ppm naphthalene acetic acid (NAA) and 0.8% agar at 15 to 20 pieces/plate and co-cultured for 2 days at 25° C. under 2000 lux condition. After the co-culturing, the pieces were cultured under sterile conditions for 7 days in MS medium (pH 5.8) comprising 3% sucrose, 0.5 ppm BAP, 0.1 ppm NAA, 250 µg/ml carbenicillin and 0.8% agar.

(3) Selection and Culturing of Transformants

After sterile culture, the pieces were transferred to MS medium (pH 5.8) comprising 3% sucrose, 0.5 ppm BAP, 0.1 ppm NAA, 250 µg/ml carbenicillin, 50 µg/ml kanamycin and 0.8% agar and cultured at 25° C. under 2000 lux condition. The pieces were sub-cultured about every 2 weeks, and regeneration was observed after about 2 to 3 months from those plants that were inoculated with Agrobacterium.

The re-differentiated individuals were transferred to MS medium (pH 5.8) comprising 3% sucrose, 0.3 ppm BAP, 500 µg/ml carbenicillin and 0.8% agar, and were sub-cultured about every 2 weeks. When the re-differentiated individuals reached a size of about 3 cm, the cutting of them were inserted and planted into ½-fold MS agar medium comprising 500 µg/ml of carbenicillin and allowed to take root.

(4) Lettuce Acclimation and Seed Sampling

In the state in which the re-differentiated individuals took root and the shoots had grown to 1 to 2 cm, the shoots were cut, and the cuttings were planted and allowed to take root in vermiculite immersed in a 500-fold diluted aqueous solution of Hyponex. The plants were acclimated by gradually opening the cover of the plant box to provide ventilation. After the plants had been sufficiently acclimated, they were permanently planted in Polypot comprising Kureha Horticultural Soil (Kureha engei baido) in a closed greenhouse (maximum air temperature: 30° C., natural photoperiod). Then, they were allowed to be bolting and flowering, and seeds were sampled.

EXAMPLE 3

Cloning of LBVV RNA2 Gene

Contaminated soil was sampled from a lettuce (cultivar: Cisco) field in Kagawa Prefecture, Japan that exhibited characteristic big-vein symptoms in 1997. The virus was maintained in resting spores in dry soil kept in the laboratory. Cisco, a cultivar of lettuce, was used for virus purification, and the virus was inoculated by regular transfer in soil.

Virus purification and RNA purification were carried out in accordance with Example 1. Synthesis of cDNA and determination of nucleotide sequence were carried out in accordance with the method of C. F. Fazeli & M. A. Rezaian (Journal of General Virology, 81, 605-615) using a genome walking method, in which the sequence is extended by synthesizing primer to the downstream direction. First, virus-specific 5LB5R3 primer (AGCTCTGAACAACGA-CATG/SEQ ID NO: 16) was produced based on Example 1, and a first cDNA was synthesized with SUPERSCRIPT™ II RNase H⁻ Reverse Transcriptase using an RNA from the purified LBVV as a template. Next, a second cDNA was synthesized with Klenow Fragment (Takara) using universal primer dN6 (5'-GCCGGAGCTCTGCAGAAT-TCNNNNNN-3'/SEQ ID NO: 14). After removing excess primer with the GlassMax DNA Isolation Spin Cartridge System (Gibco BRL), PCR was carried out using the virus-specific primer and universal primer (5'-GCCGGAGCTCT-GCAGAATTC-3'/SEQ ID NO: 15) and the resulting PCR product was cloned using pGEM®-T Easy Vector Systems. Then, the nucleotide sequence was determined. The same procedure was then repeated four times to determine up to 5177 nucleotides. Determination of the 3'-terminus of RNA2 was carried out by 5'RACE (Note: since purified LBVV RNA contains both a positive-strand and a negative-strand, not only the 5'-terminus but also 3'-terminus can be determined by 5'RACE), and a 6078 nucleotides sequence was determined that comprised genes for five proteins encoded by LBVV (SEQ ID NO: 1). Furthermore, the 500- to 700-bp PCR products from RNA2 were recloned using mutually overlapping virus specific primers. At least three clones were sequenced from each region, and the nucleotide sequence of RNA2 was confirmed.

A 6078 nucleotides sequence was determined using the above method. This gene encoded five proteins. Protein 1 (coat protein: Example 1) had a translation initiation site at nucleotide 209 and encoded 397 amino acids (SEQ ID NO: 2), protein 2 had a translation initiation site at nucleotide 1492 and encoded 333 amino acids (SEQ ID NO: 3), protein 3 had a translation initiation site at nucleotide 2616 and encoded 290 amino acids (SEQ ID NO: 4), protein 4 had a translation initiation site at nucleotide 3842 and encoded 164 amino acids (SEQ ID NO: 5), and protein 5 had a translation initiation site at nucleotide 4529 and encoded 368 amino acids (SEQ ID NO: 6). When the homology of the amino acid sequences was compared with other viruses, only protein 1 (coat protein) was observed to be homologous to the nucleocapsid protein (coat protein) of viruses belonging to the family Rhabdoviridae.

EXAMPLE 4

Cloning of LBVV Polymerase Gene

Contaminated soil was sampled from a lettuce (cultivar: Cisco) field in Kagawa Prefecture, Japan that exhibited characteristic big-vein symptoms in 1997. The virus was maintained in resting spores in dry soil kept in the laboratory. Cisco, a cultivar of lettuce, was used for virus purification, and the virus was inoculated by regular transfer in soil.

Virus purification was carried out in the same manner as the procedure for virus purification of Example 1. Extraction of highly pure LBVV RNA was carried out in the manner described below. After treatment of the purified virus with Proteinase K-SDS, it was extracted with phenol/chloroform and precipitated with ethanol. Next, after the viral nucleic acid was treated with DNase and further purified with The RNaid® Kit (BIO 101), a 7.3 kb RNA of two LBVV RNAs was isolated by 1% agarose gel (SeaPlaque GTG agarose, FMC) electrophoresis and used for synthesis of cDNA. Synthesis of cDNA was carried out in accordance with the method of P. Froussard (Nucleic Acids Research, 20, 2900). In brief, a first cDNA was synthesized with the SUPER-SCRIPT™ II RNase H⁻ Reverse Transcriptase using universal primer-dN6 (5'-GCCGGAGCTCTGCAGAAT-TCNNNNNN-3'/SEQ ID NO: 14). Next, a second cDNA was synthesized with Klenow Fragment, PCR was carried out using universal primer (5'-GCCGGAGCTCTGCA-GAATTC-3'/SEQ ID NO: 15), and the resulting PCR product was cloned using pGEM®-T Easy Vector Systems Then, the nucleotide sequence was determined.

Eight partial LBVV polymerase gene fragments of about 500 bp were obtained. Both terminals of the polymerase gene were filled by 5'RACE and the gaps between the fragments were filled in by RT-PCR, thereby determining a 6793 nucleotides sequence that contained the full-length polymerase gene (SEQ ID NO: 12). Furthermore, the 500- to 700-bp PCR products from polymerase gene were recloned using mutually overlapping virus-specific primers. At least three clones were sequenced from each region, and the nucleotide sequence of polymerase gene was confirmed.

This gene encoded 2040 amino acids with a translation initiation site at nucleotide 337 (SEQ ID NO: 13). When the homology of the amino acid sequence was compared with other viruses, it was confirmed that the protein is homologous to the polymerases of viruses belonging to the family Mononegavirales, especially, viruses belonging to the family Rhabdoviridae, and retained four motifs considered to be responsible for polymerase activity.

INDUSTRIAL APPLICABILITY

According to the present invention, nucleic acids encoding proteins of LBVV were isolated, and their primary structure was elucidated. It therefore became possible to produce a lettuce plant having resistance to the virus by expressing the nucleic acid or its antisense nucleic acid in lettuce. In addition, it became possible to make a diagnosis of infection with LBVV by detecting the nucleic acid or protein encoded thereby.

The invention claimed is:

1. An isolated nucleic acid encoding a coat protein of lettuce big-vein virus, said nucleic acid selected from the group consisting of:

(a) a nucleic acid encoding a protein comprising the amino acid sequence of SEQ ID NO: 2; and (b) the nucleic acid of (a) comprising bases 209-1400 of the nucleotide sequence of SEQ ID NO:1.

2. The nucleic acid according to claim 1, wherein the nucleic acid is an RNA.

3. The nucleic acid according to claim 1, wherein the nucleic acid is a DNA.

4. An isolated DNA encoding an RNA that suppresses the production of a lettuce big-vein virus protein comprising the amino acid sequence of SEQ ID NO: 2, wherein the DNA is any one of the following (a) to (d):

(a) a DNA encoding a sense RNA which has a complementarity of 90% or more to RNA that is completely complementary to the RNA according to claim 2;

(b) a DNA encoding an antisense RNA which has a complementarity of 90% or more to the RNA according to claim 2;

(c) a DNA encoding the RNA according to claim 2; and (d) a DNA encoding an antisense RNA which is completely complementary to the RNA according to claim 2.

5. A vector comprising the nucleic acid according to claim 3.

6. A transformed cell comprising the nucleic acid according to claim 3.

7. A method of producing a protein, wherein said method comprises the steps of:

(a) culturing the transformed cell of claim 6; and (b) recovering an expressed protein from said transformed cell or its culture supernatant.

8. A vector comprising the DNA according to claim 4.

9. A transformed lettuce cell that comprises the nucleic acid according to claim 1.

10. A transformed lettuce cell that comprises the DNA according to claim 4.

11. A transformed lettuce cell that comprises the vector according to claim 5 or claim 8.

12. A transformed lettuce plant comprising the transformed lettuce cell according to claim 9 or claim 10.

13. A transformed lettuce plant comprising the transformed lettuce cell according to claim 11.

14. A transformed lettuce plant that is a progeny or a clone of the transformed lettuce plant according to claim 12.

15. A transformed lettuce plant that is a progeny or a clone of the transformed lettuce plant according to claim 13.

16. A propagation material of the transformed lettuce plant according to claim 12, wherein the propagation material comprises said nucleic acid.

17. A propagation material of the transformed lettuce plant according to claim 13, wherein the propagation material comprises said nucleic acid.

18. A propagation material of the transformed lettuce plant according to claim 14, wherein the propagation material comprises said nucleic acid.

19. A propagation material of the transformed lettuce plant according to claim 15, wherein the propagation material comprises said nucleic acid.

20. A transformed cell comprising the vector according to claim 5.

21. A method of producing a protein, wherein said method comprises the steps of:

(a) culturing the transformed cell of claim 20; and (b) recovering an expressed protein from said transformed cell or its culture supernatant.

* * * * *